US009613402B2

(12) United States Patent
Takahashi

(10) Patent No.: US 9,613,402 B2
(45) Date of Patent: Apr. 4, 2017

(54) IMAGE PROCESSING DEVICE, ENDOSCOPE SYSTEM, IMAGE PROCESSING METHOD, AND COMPUTER-READABLE STORAGE DEVICE

(71) Applicant: OLYMPUS CORPORATION, Shibuya-ku, Tokyo (JP)

(72) Inventor: Jumpei Takahashi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 410 days.

(21) Appl. No.: 14/226,597

(22) Filed: Mar. 26, 2014

(65) Prior Publication Data
US 2014/0210973 A1 Jul. 31, 2014

Related U.S. Application Data

(63) Continuation of application No. PCT/JP2012/075611, filed on Oct. 3, 2012.

(30) Foreign Application Priority Data

Oct. 4, 2011 (JP) .................................. 2011-219817

(51) Int. Cl.
*G06T 5/00* (2006.01)
*G06T 7/20* (2017.01)
(Continued)

(52) U.S. Cl.
CPC .......... *G06T 5/002* (2013.01); *A61B 1/00009* (2013.01); *A61B 1/04* (2013.01);
(Continued)

(58) Field of Classification Search
CPC ...... H04N 5/23251; G06T 2207/10068; G06T 5/002; G06T 7/2053
See application file for complete search history.

(56) References Cited

U.S. PATENT DOCUMENTS 5,404,178 A 4/1995 Kondo et al.
7,145,607 B1 12/2006 Hui
(Continued)

FOREIGN PATENT DOCUMENTS

EP 0592196 A2 4/1994
EP 2216984 A1 8/2010
(Continued)

OTHER PUBLICATIONS

Extended European Search Report (EESR) dated Apr. 16, 2015 issued in counterpart European Application No. 12838593.7.
(Continued)

*Primary Examiner* — Obafemi Sosanya
(74) *Attorney, Agent, or Firm* — Holtz, Holtz & Volek PC

(57) ABSTRACT

An image processing device includes an evaluation value calculation section that calculates an evaluation value that is used to determine whether or not an inter-frame state of an object within a captured image is a stationary state, an estimated noise amount acquisition section that acquires an estimated noise amount of the captured image, a determination section that determines whether or not the inter-frame state of the object is the stationary state based on the evaluation value and the estimated noise amount, and a noise reduction processing section that performs a first noise reduction process (time-direction noise reduction process) when it has been determined that the inter-frame state of the object is the stationary state, and performs a second noise reduction process that includes at least a spatial-direction noise reduction process when it has been determined that the inter-frame state of the object is not the stationary state.

20 Claims, 19 Drawing Sheets

(51) Int. Cl.
*A61B 1/04* (2006.01)
*A61B 1/00* (2006.01)
*G06K 9/40* (2006.01)

(52) U.S. Cl.
CPC ........ *G06T 7/2053* (2013.01); *A61B 1/00186* (2013.01); *G06T 2207/10016* (2013.01); *G06T 2207/10024* (2013.01); *G06T 2207/10068* (2013.01)

(56) References Cited

U.S. PATENT DOCUMENTS

| | | |
|---|---|---|
| 2005/0280739 A1 | 12/2005 | Lin et al. |
| 2007/0236609 A1 | 10/2007 | Pathak et al. |
| 2008/0294056 A1* | 11/2008 | Boutet ................. A61B 5/0059 600/476 |
| 2009/0158315 A1* | 6/2009 | Bendall ................. H04N 7/185 725/32 |
| 2010/0188535 A1 | 7/2010 | Mitsuya et al. |
| 2010/0195926 A1* | 8/2010 | Sasaki ..................... G06K 9/40 382/260 |
| 2010/0225790 A1 | 9/2010 | Sasaki |
| 2013/0258080 A1 | 10/2013 | Kuriyama |

FOREIGN PATENT DOCUMENTS

| | | |
|---|---|---|
| EP | 2647331 A1 | 10/2013 |
| JP | 02-013069 A | 1/1990 |
| JP | 06-047036 A | 2/1994 |
| JP | 06-121192 A | 4/1994 |
| JP | 2009-130537 A | 6/2009 |
| JP | 2009-533898 A | 9/2009 |
| JP | 2010-171808 A | 8/2010 |
| JP | 2011-124694 A | 6/2011 |
| WO | 0135636 A1 | 5/2001 |
| WO | 2007117623 A2 | 10/2007 |

OTHER PUBLICATIONS

Liang Ma, et al., "Noise Reduction of Video Sequences Using Detection Method", 2009 International Conference on Education Technology and Computer, pp. 299-302.

International Search Report (ISR) dated Dec. 25, 2012 (and English translation thereof) issued in International Application No. PCT/JP2012/075611.

* cited by examiner

| g | r | g | r | g | r |
| b | g | b | g | b | g |
| g | r | g | r | g | r |
| b | g | b | g | b | g |

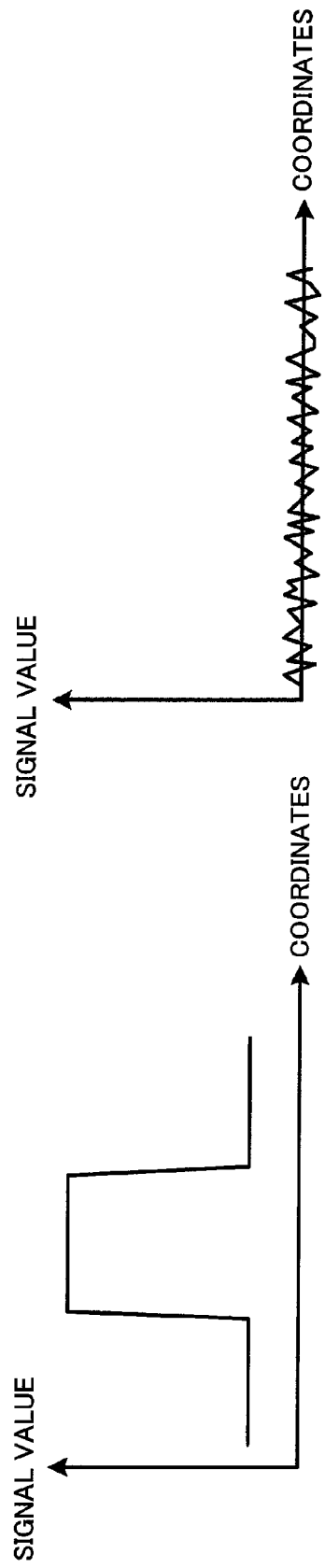

IMAGE PROCESSING DEVICE, ENDOSCOPE SYSTEM, IMAGE PROCESSING METHOD, AND COMPUTER-READABLE STORAGE DEVICE

CROSS REFERENCE TO RELATED APPLICATION

This application is a continuation of International Patent Application No. PCT/JP2012/075611, having an international filing date of Oct. 3, 2012, which designated the United States, the entirety of which is incorporated herein by reference. Japanese Patent Application No. 2011-219817 filed on Oct. 4, 2011 is also incorporated herein by reference in its entirety.

BACKGROUND

The present invention relates to an image processing device, an endoscope system, an image processing method, a computer-readable storage device, and the like.

A noise reduction process (NR process) is roughly classified into a spatial-direction NR process that reduces noise within the processing target frame and a time-direction NR process that reduces noise using the processing target frame and the preceding frame.

The spatial-direction NR process has a tendency in which a high-frequency component of the image is attenuated, and the time-direction NR process has a tendency in which a residual image occurs when the object makes a motion. Therefore, it has been desired to implement a sophisticated NR process by adaptively selecting the spatial-direction NR process when the image is stationary.

JP-A-6-47036 discloses a technique that determines whether the state of the image is a stationary state or a moving state, and adaptively switches the NR process between the time-direction NR process and the spatial-direction NR process corresponding to the determination result. In JP-A-6-47036, the state of the image is determined to be the stationary state when the inter-frame difference value (i.e., a difference value calculated between frames) is smaller than a threshold value, and determined to be the moving state when the inter-frame difference value is larger than the threshold value.

SUMMARY

According to one aspect of the invention, there is provided an image processing device comprising:

an evaluation value calculation section that calculates an evaluation value that is used to determine whether or not an inter-frame state of an object within a captured image is a stationary state;

an estimated noise amount acquisition section that acquires an estimated noise amount of the captured image;

a determination section that determines whether or not the inter-frame state of the object is the stationary state based on the evaluation value, the estimated noise amount, and a specific condition; and a noise reduction processing section that performs a first noise reduction process that is a time-direction noise reduction process on the captured image when it has been determined that the inter-frame state of the object is the stationary state, and performs a second noise reduction process that includes at least a spatial-direction noise reduction process on the captured image when it has been determined that the inter-frame state of the object is not the stationary state, the specific condition being an observation state of the object, or whether a target area of a noise reduction process belongs to a front-field-of-view area or a side-field-of-view area, or a type of the captured image.

According to another aspect of the invention, there is provided an endo scope system comprising:

an imaging section that captures a captured image;

an evaluation value calculation section that calculates an evaluation value that is used to determine whether or not an inter-frame state of an object within the captured image is a stationary state;

an estimated noise amount acquisition section that acquires an estimated noise amount of the captured image;

a determination section that determines whether or not the inter-frame state of the object is the stationary state based on the evaluation value, the estimated noise amount, and a specific condition; and a noise reduction processing section that performs a first noise reduction process that is a time-direction noise reduction process on the captured image when it has been determined that the inter-frame state of the object is the stationary state, and performs a second noise reduction process that includes at least a spatial-direction noise reduction process on the captured image when it has been determined that the inter-frame state of the object is not the stationary state, the specific condition being an observation state of the object, or whether a target area of a noise reduction process belongs to a front-field-of-view area or a side-field-of-view area, or a type of the captured image.

According to another aspect of the invention, there is provided an image processing method comprising:

calculating an evaluation value that is used to determine whether or not an inter-frame state of an object within a captured image is a stationary state;

acquiring an estimated noise amount of the captured image;

determining whether or not the inter-frame state of the object is the stationary state based on the evaluation value, the estimated noise amount, and a specific condition, the specific condition being an observation state of the object, or whether a target area of a noise reduction process belongs to a front-field-of-view area or a side-field-of-view area, or a type of the captured image; and performing a first noise reduction process that is a time-direction noise reduction process on the captured image when it has been determined that the inter-frame state of the object is the stationary state, and performing a second noise reduction process that includes at least a spatial-direction noise reduction process on the captured image when it has been determined that the inter-frame state of the object is not the stationary state.

According to another aspect of the invention, there is provided a computer-readable storage device with an executable program stored thereon, wherein the program instructs a computer to perform steps of:

calculating an evaluation value that is used to determine whether or not an inter-frame state of an object within a captured image is a stationary state;

acquiring an estimated noise amount of the captured image;

determining whether or not the inter-frame state of the object is the stationary state based on the evaluation value and the estimated noise amount; and performing a first noise reduction process that is a time-direction noise reduction process on the captured image when it has been determined that the inter-frame state of the object is the stationary state, and performing a second noise reduction process that includes at least a spatial-direction noise reduction process on the captured image when it has been determined that the inter-frame state of the object is not the stationary state.

BRIEF DESCRIPTION OF THE DRAWINGS

FIG. 6A illustrates an example of a structural component included in an image signal, and FIG. 6B illustrates an example of a noise component included in an image signal.

DESCRIPTION OF EXEMPLARY EMBODIMENTS

Figure 1:
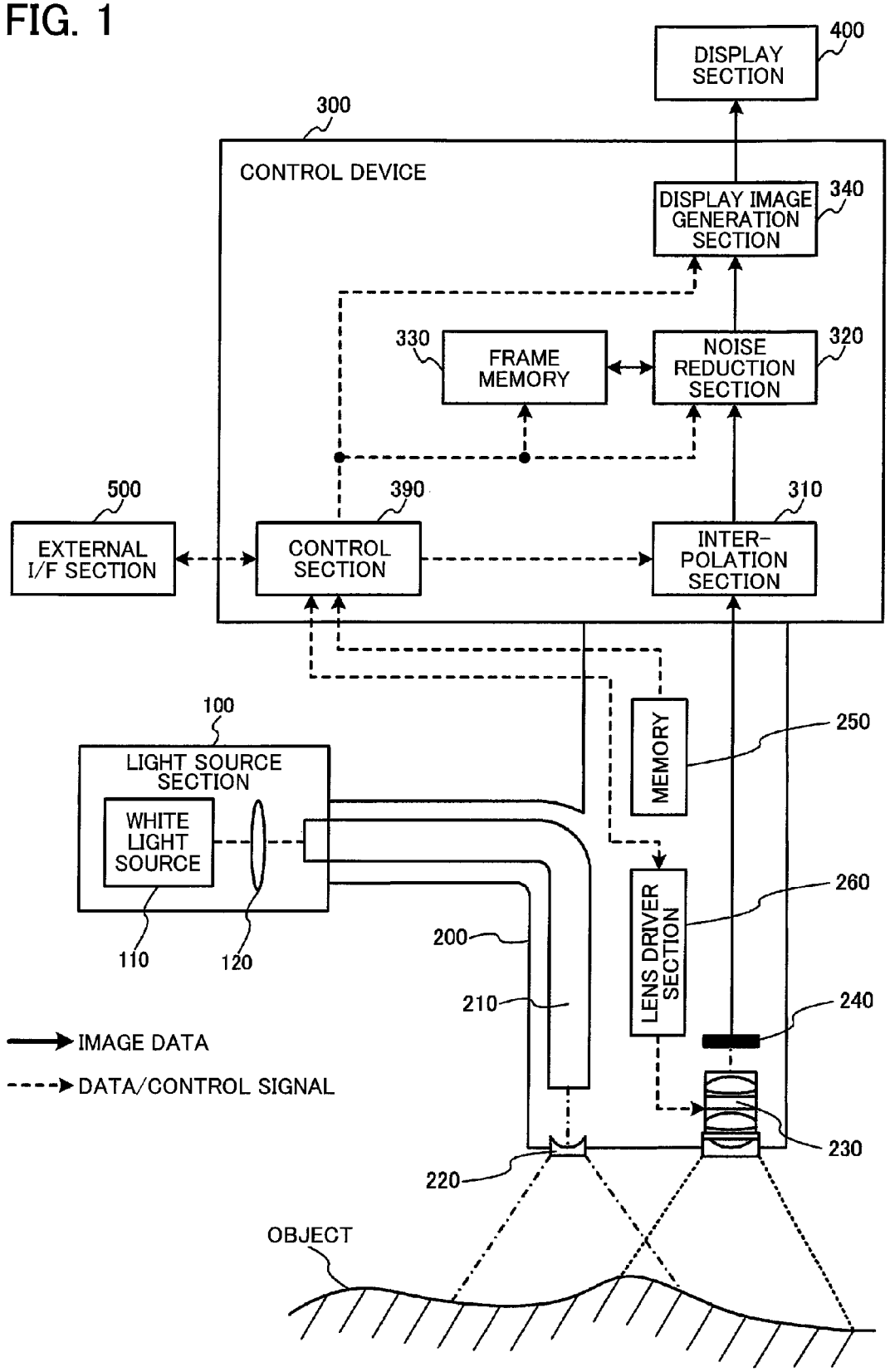
FIG. 1 illustrates a configuration example of an endoscope system according to a first embodiment.

According to one embodiment of the invention, there is provided an image processing device comprising:

an evaluation value calculation section that calculates an evaluation value that is used to determine whether or not an inter-frame state of an object within a captured image is a stationary state;

an estimated noise amount acquisition section that acquires an estimated noise amount of the captured image;

a determination section that determines whether or not the inter-frame state of the object is the stationary state based on the evaluation value and the estimated noise amount; and a noise reduction processing section that performs a first noise reduction process that is a time-direction noise reduction process on the captured image when it has been determined that the inter-frame state of the object is the stationary state, and performs a second noise reduction process that includes at least a spatial-direction noise reduction process on the captured image when it has been determined that the inter-frame state of the object is not the stationary state.

According to one embodiment of the invention, the estimated noise amount of the captured image is acquired, and whether or not the inter-frame state of the object within the captured image is the stationary state is determined based on the evaluation value and the estimated noise amount. The first noise reduction process or the second noise reduction process is performed on the captured image corresponding to the determination result. The above configuration makes it possible to accurately determine whether or not the state of the image is the stationary state.

Exemplary embodiments of the invention are described below. Note that the following exemplary embodiments do not in any way limit the scope of the invention laid out in the claims. Note also that all of the elements described below in connection with the following embodiments should not necessarily be taken as essential elements of the invention.

1. Outline

An outline of an NR process (noise reduction process) according to several embodiments of the invention is described below. Note that the term "stationary state" used herein refers to a state in which the relative positional relationship between the imaging section and the object does not change temporally. The term "moving state" used herein refers to a state in which the relative positional relationship between the imaging section and the object changes temporally.

The NR process is classified into a spatial-direction NR process and a time-direction NR process, as described above. The spatial-direction NR process reduces noise by a weighted averaging process that utilizes a pixel subjected to the NR process (processing target pixel) and its peripheral pixel. Since the spatial-direction NR process performs the weighted averaging process on the processing target pixel and its peripheral pixel, a high-frequency component of the original image necessarily attenuates.

The time-direction NR process reduces noise by a weighted averaging process that utilizes a frame subjected to the NR process (processing target frame) and a frame (preceding frame) acquired at a time differing from the acquisition time of the processing target frame. The weighted averaging process utilizes only the processing target pixel of the processing target frame, and the pixel of the preceding frame situated at the same coordinates as those of the processing target pixel. Therefore, a high-frequency component of the original image can be maintained in the stationary state. However, a residual image occurs in the moving state in which the object moves within the image.

Therefore, a sophisticated NR process can be implemented by adaptively selecting the NR process. More specifically, an NR process that can reduce only a noise component while maintaining a high-frequency component can be implemented in the stationary state by selecting the time-direction NR process in the stationary state, and selecting the spatial-direction NR process in the moving state.

However, it is difficult to accurately determine whether the state of the object is the stationary state or the moving state due to the effects of noise included in the image.

According to several embodiments of the invention, an estimated noise amount N corresponding to a pixel value is acquired. The state of the object is determined to be the stationary state when an inter-frame difference value mSAD of the image is equal to or smaller than the estimated noise amount N, and a first NR process (time-direction NR process) is performed (see FIG. 5 and the like). This makes it possible to accurately determine whether or not the object is stationary within the image, and obtain a high-resolution image when the object is stationary. When the object is not stationary, it is possible to suppress a residual image by performing a second noise reduction process that includes at least the spatial-direction noise reduction process.

2. First Embodiment

2.1. Endoscope System

A first embodiment of the invention is described below. FIG. 1 illustrates a configuration example of an endoscope system according to the first embodiment. The endoscope system (endoscope apparatus) includes a light source section 100, an imaging section 200, a control device 300, a display section 400, and an external I/F section 500. The control device 300 includes an interpolation section 310, a noise reduction section 320, a frame memory 330, a display image generation section 340, and a control section 390.

The light source section 100 includes a white light source 110 that emits white light, and a condenser lens 120 that focuses the white light on a light guide fiber 210.

The imaging section 200 is formed to be elongated and flexible (i.e., can be curved) so that the imaging section 200 can be inserted into a body cavity or the like. The imaging section 200 is removable from the control device 300 since a different imaging section is used depending on the observation area. Note that the imaging section 200 is hereinafter appropriately referred to as "scope".

The imaging section 200 includes the light guide fiber 210 that guides the light focused by the light source section 100, and an illumination lens 220 that diffuses the light guided by the light guide fiber 210 to illuminate an object. The imaging section 200 also includes a condenser lens 230 that focuses reflected light from the object, an image sensor 240 that detects the reflected light focused by the condenser lens 230, a memory 250, and a lens driver section 260 that drives a zoom lens included in the condenser lens 230.

The memory 250 is connected to the control section 390. The lens driver section 260 is bidirectionally connected to the control section 390.

Figures 2, 3:
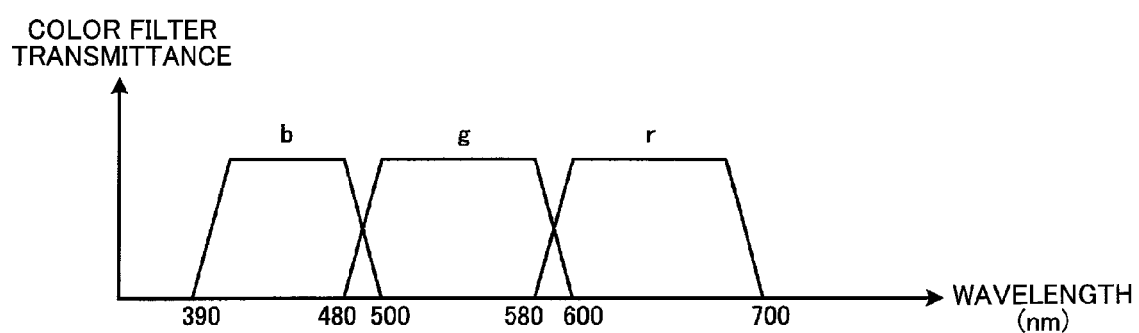
FIG. 2 illustrates a configuration example of the arrangement of color filters included in an image sensor.
FIG. 3 illustrates an example of the transmittance characteristics of color filters included in an image sensor.

The image sensor 240 has a Bayer color filter array illustrated in FIG. 2. The color filters include an r filter, a g filter, and a b filter. As illustrated in FIG. 3, the r filter allows light having a wavelength of 580 to 700 nm to pass through, the g filter allows light having a wavelength of 480 to 600 nm to pass through, and the b filter allows light having a wavelength of 390 to 500 nm to pass through.

The memory 250 stores an identification number of each scope. The control section 390 can determine the type of the connected scope referring to the identification number stored in the memory 250.

The condenser lens 230 is configured so that the angle of view θ can be set within the range of $\theta_{MIN}$ to $\theta_{MAX}$ (deg). In the first embodiment, a state in which the angle of view θ is $\theta_{MAX}$ is referred to as "normal observation state", and a state in which the angle of view θ is smaller than $\theta_{MAX}$ is referred to as "zoom observation state". The user can set an arbitrary angle of view θ using the external I/F section 500. When the user has set the angle of view θ, the angle of view θ set by the user is input to the control section 390, and the control section 390 (angle-of-view control section in a narrow sense) transmits the angle of view θ to the lens driver section 260. The lens driver section 260 drives the zoom lens included in the condenser lens 230 so that the angle of view of the imaging section 200 is set to the desired angle of view θ. The control section 390 also outputs the angle of view θ set by the user to the noise reduction section 320.

The external I/F section 500 is an interface that allows the user to input information and the like to the endoscope system. For example, the external I/F section 500 includes a power switch (power ON/OFF switch), a mode (e.g., imaging mode) switch button, and the like. The external I/F section 500 outputs the input information to the control section 390.

The control device 300 controls each element of the endoscope system, and performs image processing and the like on the captured image. The interpolation section 310 is connected to the noise reduction section 320. The noise reduction section 320 is connected to the display image generation section 340. The noise reduction section 320 is bidirectionally connected to the frame memory 330. The display image generation section 340 is connected to the display section 400. The control section 390 is connected to the interpolation section 310, the noise reduction section 320, the frame memory 330, and the display image generation section 340, and controls the interpolation section 310, the noise reduction section 320, the frame memory 330, and the display image generation section 340.

The interpolation section 310 performs an interpolation process on the image acquired by the image sensor 240. Since the image sensor 240 has a Bayer array, each pixel of the image acquired by the image sensor 240 has an R, G, or B signal value (i.e., two signal values among the R, G, and B signal values are missing). The interpolation section 310 interpolates the missing signal values by performing the interpolation process on each pixel of the image to generate an image in which each pixel has the R, G, and B signal values. A known bicubic interpolation process may be used as the interpolation process, for example. Note that the image obtained by the interpolation process is hereinafter referred to as "RGB image". The interpolation section 310 outputs the generated RGB image to the noise reduction section 320.

The noise reduction section 320 performs an NR process on the RGB image output from the interpolation section 310. The noise reduction section 320 determines whether the state of the object in each pixel of the RGB image is a stationary state or a moving state, and adaptively switches the NR process corresponding to the determination result. More specifically, the noise reduction section 320 selects a time-direction NR process that can maintain a high-frequency component when it has been determined that the state of the object is the stationary state, and selects a spatial-direction NR process when it has been determined that the state of the object is the moving state. This makes it possible to reduce only noise while maintaining a high-frequency component when the state of the object is the stationary state, and implement a sophisticated NR process. The details of the noise reduction section 320 are described later. Note that the image obtained by the NR process is hereinafter referred to as "NR image (noise-reduced image)".

The display image generation section 340 performs a white balance process, a color conversion process, a gray-scale conversion process, and the like on the NR image output from the noise reduction section 320 to generate a display image. The display image generation section 340 outputs the display image to the display section 400. The display section 400 is implemented by a display such as a liquid crystal display.

2.2. Noise Reduction Process

Figure 4:
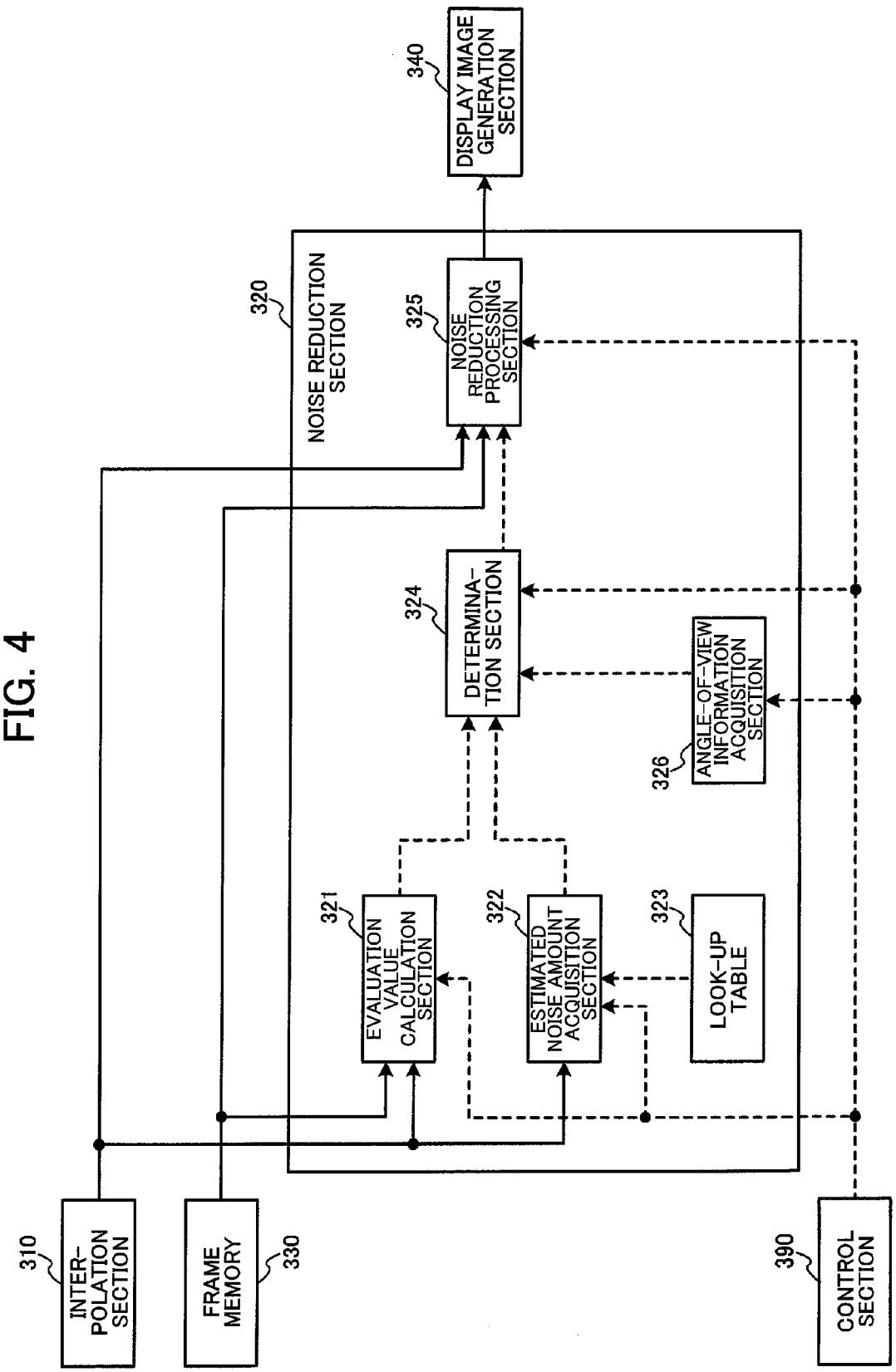
FIG. 4 illustrates a detailed configuration example of a noise reduction section according to the first embodiment.

The noise reduction section 320 is described in detail below. FIG. 4 illustrates a detailed configuration example of the noise reduction section 320 according to the first embodiment. The noise reduction section 320 includes an evaluation value calculation section 321, an estimated noise amount acquisition section 322, a look-up table 323, a determination section 324, a noise reduction processing section 325, and an angle-of-view information acquisition section 326.

Figure 5:
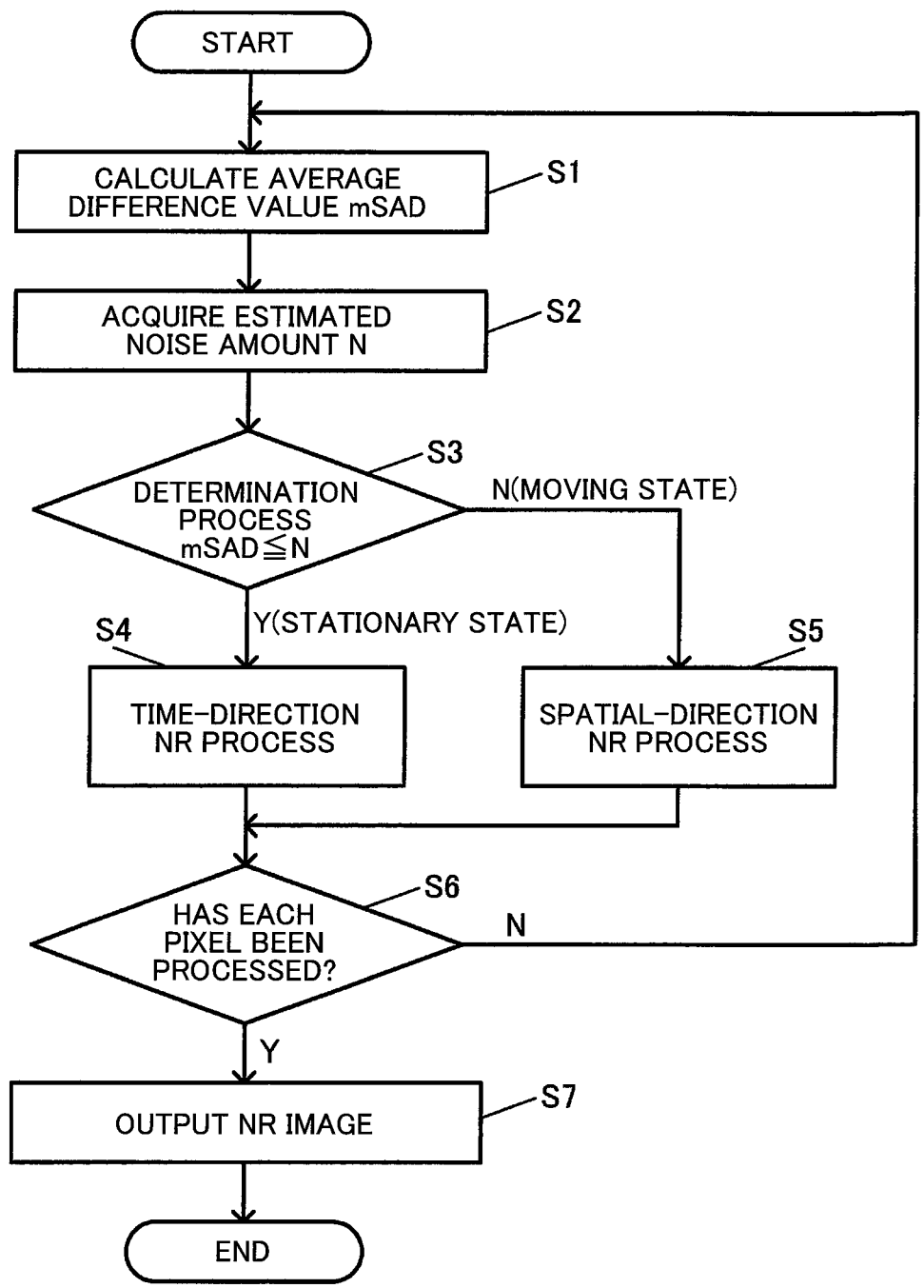
FIG. 5 is a flowchart illustrating a noise reduction process according to the first embodiment.

FIG. 5 is a flowchart illustrating the noise reduction process according to the first embodiment. In a step S1, the evaluation value calculation section 321 calculates an average difference value mSAD using the RGB image output from the interpolation section 310 and a preceding image stored in the frame memory 330. The term "preceding image" used herein refers to the NR image output from the noise reduction section 320 prior to the RGB image by one frame.

The coordinates of an attention pixel that is a pixel subjected to the NR process are referred to as (x, y). The average difference value mSAD (inter-frame difference value) is calculated using the following expression (1). The evaluation value calculation section 321 outputs the values (m, n) that minimize the SAD(m, n) in the expression (1) to the noise reduction processing section 325. The process performed on the G signal is described below. Note that the same process is also performed on the R signal and the B signal.

$$mSAD = \min \begin{Bmatrix} SAD(-1,-1), & SAD(0,-1), & SAD(1,-1) \\ SAD(-1,0), & SAD(0,0), & SAD(1,0), \\ SAD(-1,1), & SAD(0,1), & SAD(1,1), \end{Bmatrix} \quad (1)$$

$$SAD(m, n) =$$

$$\frac{1}{(2k+1)^2} \sum_{j=-k}^{k} \sum_{i=-k}^{k} \|F_{G\_cur}(x+i, y+j) - F_{G\_pre}(x+i+m, y+j+n)\|$$

where, min( ) is a process that acquires a minimum of the value in the parentheses, m=−1, 0, or 1, n=−1, 0, or 1, $F_{G\_cur}(x, y)$ is the G signal value of the RGB image at the coordinates (x, y), $F_{G\_pre}(x, y)$ is the G signal value of the preceding image at the coordinates (x, y), k is a natural number, (2k+1) corresponds to the kernel size when calculating the average difference value mSAD, provided that k may be a value set in advance, or may be an arbitrary value set by the user via the external I/F section 500, and ‖A‖ is a process that acquires the absolute value of a real number A.

The features of the average difference value mSAD in each of the stationary state and the moving state are described below. Note that an image is handled as one-dimensional signals for convenience of explanation. The image signal includes the structural component illustrated in FIG. 6A and the noise component illustrated in FIG. 6B.

Figure 7A:
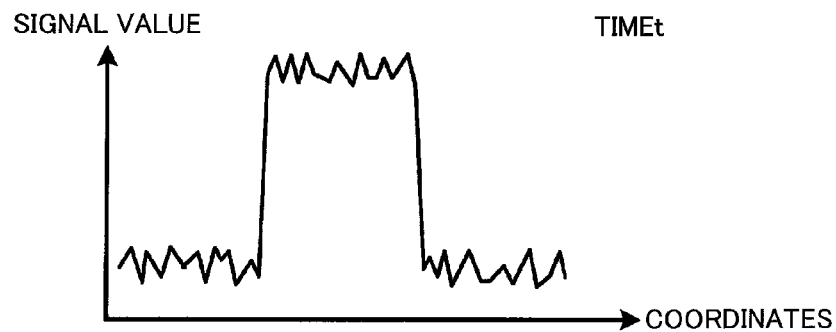
FIGS. 7A to 7C are views illustrating an inter-frame difference value mSAD.
Figure 7B:
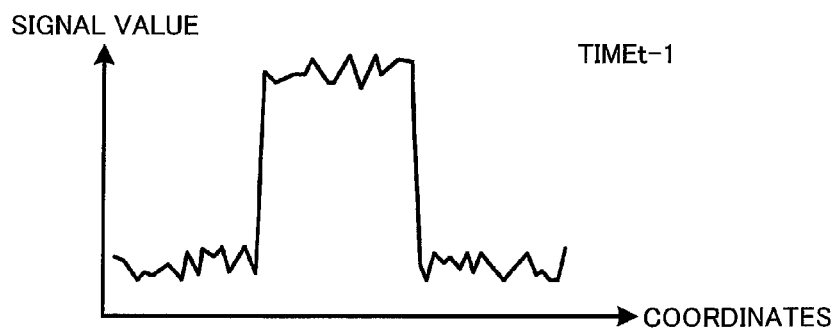
Figure 7C:
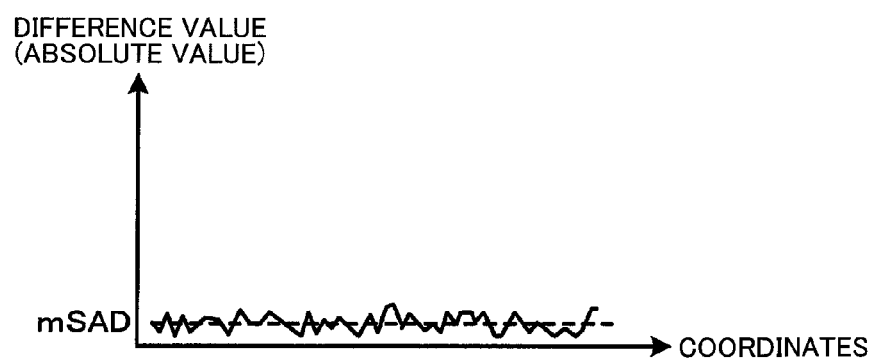

For example, the image illustrated in FIG. 7A is acquired at a time t, and the image illustrated in FIG. 7B is acquired at a time t−1 immediately before the time t. In this case, the position of the structural component is identical at the time t and the time t−1 (corresponding to the stationary state). Therefore, the difference value (i.e., the absolute value of the difference value) between the image at the time t and the image at the time t−1 includes only the noise component (see FIG. 7C).

Figure 8A:
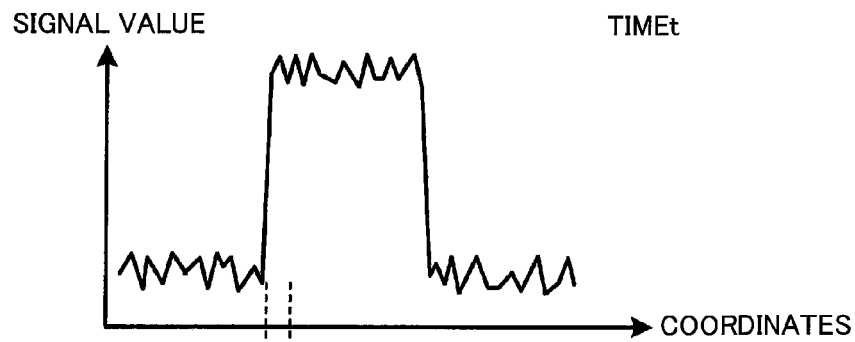
FIGS. 8A to 8C are views illustrating an inter-frame difference value mSAD.
Figure 8B:
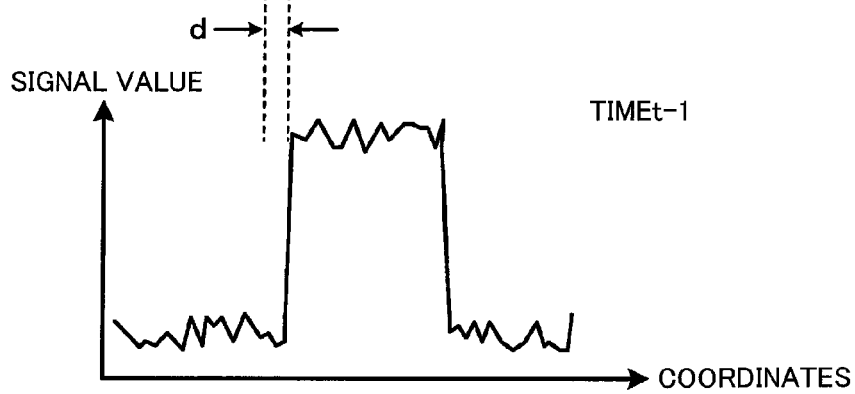
Figure 8C:
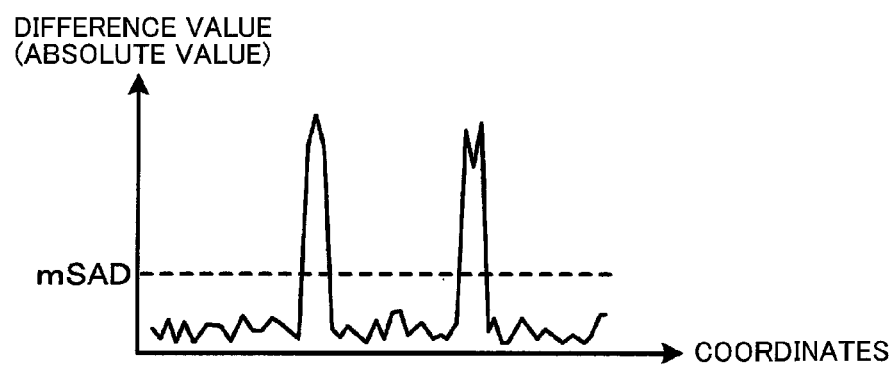

Alternatively, the image illustrated in FIG. 8A is acquired at the time t, and the image illustrated in FIG. 8B is acquired at the time t−1 immediately before the time t. d in FIG. 8B corresponds to the inter-frame motion amount of the object (corresponding to the moving state). In this case, the difference value between the image at the time t and the image at the time t−1 includes both the noise component and the structural component (see FIG. 8C).

Specifically, the average difference value mSAD in the moving state is larger than the average difference value mSAD in the stationary state. Therefore, whether the state of the object is the stationary state or the moving state can be determined by utilizing the average difference value mSAD (=noise amount) in the stationary state as a threshold value.

Figure 9:
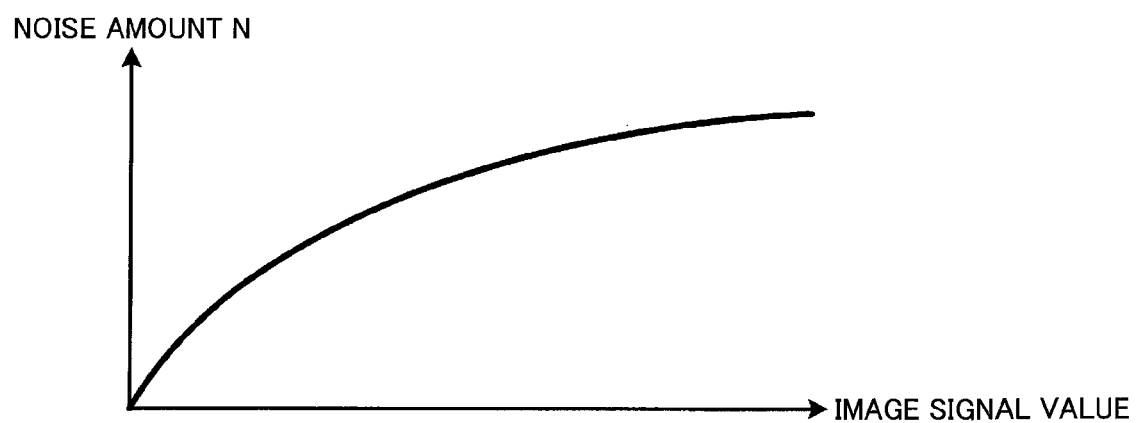
FIG. 9 illustrates an example of the characteristic of the amount of noise included in an image.

However, the noise amount normally changes depending on the image signal value (see FIG. 9). Specifically, the noise amount increases as the image signal value increases. Therefore, the average difference value mSAD in the stationary state (see FIG. 7C) also changes depending on the image signal value. When a fixed threshold value is used to determine whether the state of the object is the stationary state or the moving state, it is difficult to accurately determine whether the state of the object is the stationary state or the moving state due to the noise dependence of the average difference value mSAD.

In the first embodiment, the characteristics of the noise amount illustrated in FIG. 9 are stored as a table (noise amount table), and the noise amount N corresponding to the signal value of each pixel is acquired referring to the table. Whether the state of the object is the stationary state or the moving state is determined based on the noise amount N. This makes it possible to implement a highly accurate determination.

(m, n) in the expression (1) corresponds to the inter-frame motion vector, and the motion vector search range is ±1 pixel. In the expression (1), a minimum value SAD within the search range is selected as the average difference value mSAD. Therefore, even when a motion has occurred between the RGB image and the preceding image by about ±1 pixel, the time-direction NR process is selected (step S3 (described later)). When the motion amount (m, n) is larger than 1 pixel, the spatial-direction NR process is selected (step S3 (described later)) since a correct motion vector (m, n) cannot be calculated.

Since a minute motion is present even when the object is stationary within the image, the spatial-direction NR process is selected even in a substantially stationary state, and the amount of structural component of the image decreases when the state of the object is strictly determined to be the moving state. According to the expression (1), since the state of the object is determined to be the stationary state when the motion amount is ±1 pixel, a high-resolution image can be obtained by the time-direction NR process.

In a step S2 in FIG. 5, the estimated noise amount acquisition section 322 acquires the noise amount N. Specifically, the characteristics of the noise amount N described above with reference to FIG. 9 are stored in the look-up table 323 (noise amount table). The estimated noise amount acquisition section 322 acquires the noise amount N corresponding to the signal value of the attention pixel (processing target pixel) of the RGB image referring to the look-up table 323.

The noise amount table differs depending on the connected scope. Since the identification number of each scope is stored in the memory 250 included in the imaging section 200, the connected scope can be determined. Specifically, the control section 390 acquires the identification number stored in the memory 250 to determine the connected scope, and outputs the determination result to the noise reduction section 320. The estimated noise amount acquisition section 322 acquires the noise amount N referring to the noise amount table corresponding to the scope.

In a step S3 in FIG. 5, the determination section 324 performs a determination process that determines whether the state of the object is the stationary state or the moving state using the average difference value mSAD output in the step S1 and the noise amount N output in the step S2. Specifically, the determination section 324 performs the determination process using the following expression (2).

$$\text{if } mSAD \leq N \quad \text{stationary state} \tag{2}$$
$$\text{else} \quad \text{moving state}$$

The noise reduction processing section 325 performs the time-direction NR process (first noise reduction process in a broad sense) when it has been determined that the state of the object is the stationary state in the step S3 (step S4). The noise reduction processing section 325 performs the spatial-direction NR process (second noise reduction process in a broad sense) when it has been determined that the state of the object is the moving state in the step S3 (step S5). The details of the time-direction NR process and the spatial-direction NR process are described later.

In a step S6, whether or not the NR process has been performed on all of the pixels of the RGB image is determined. When it has been determined that the NR process has been performed on all of the pixels of the RGB image, the noise reduction section 320 outputs the NR image to the frame memory 330 and the display image generation section 340 (step S7) to complete the process. The frame memory 330 stores the NR image output from the noise reduction section 320 as the preceding image. When it has been determined that the NR process has not been performed on all of the pixels of the RGB image, the steps S1 to S6 are repeated.

2.3. Noise Reduction Process Corresponding to Observation State

A method that changes the threshold value used to determine whether or not the state of the object is the stationary state or the moving state corresponding to whether or not the observation state is the zoom observation state is described below.

Figure 10:
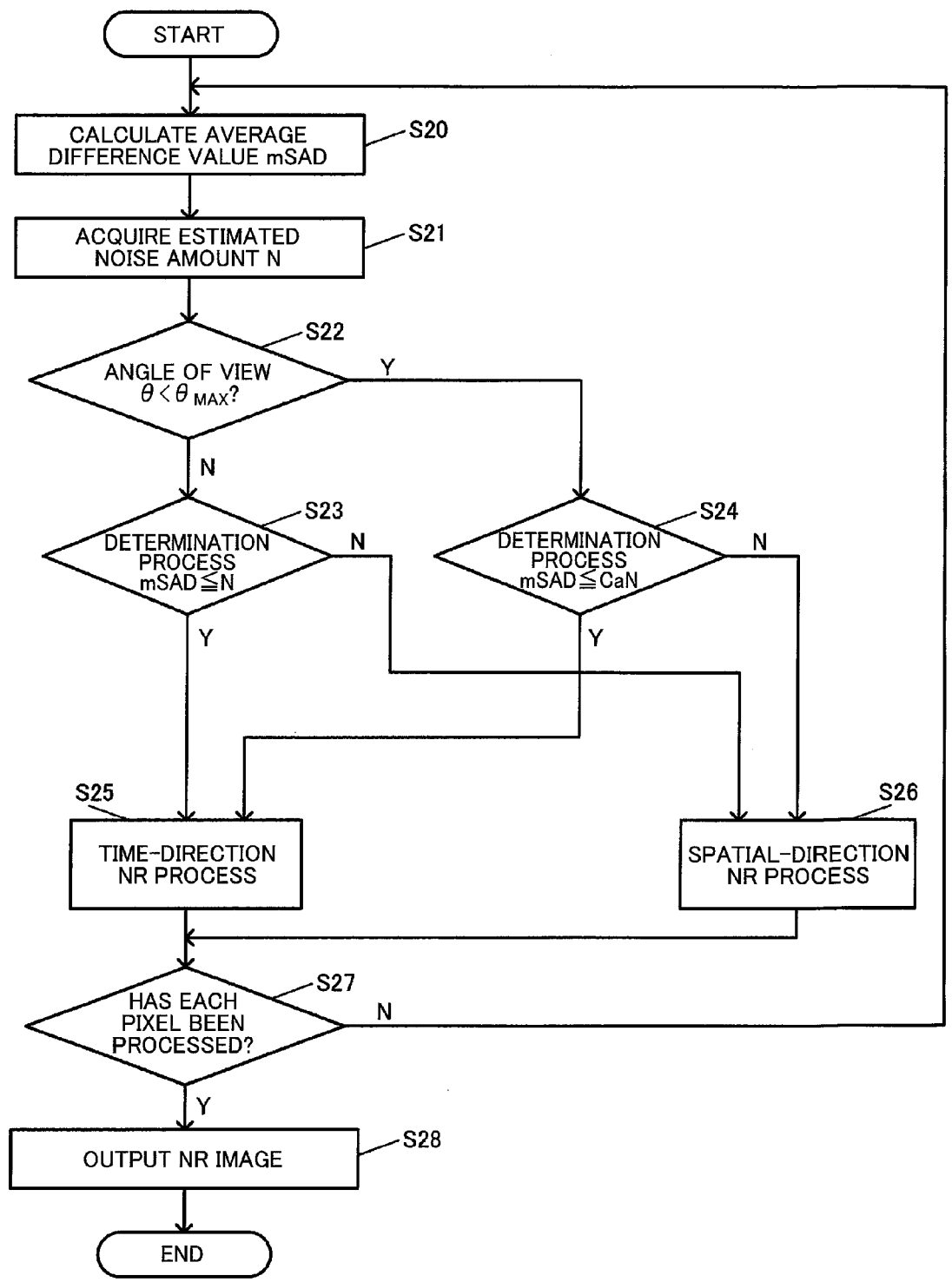
FIG. 10 is a second flowchart illustrating the noise reduction process according to the first embodiment.

FIG. 10 is a second flowchart illustrating the noise reduction process according to the first embodiment. Note that the steps other than steps S22 and S24 are the same as the steps S1 to S7 illustrated in FIG. 5, and description thereof is appropriately omitted. In the step S22, the angle-of-view information acquisition section 326 acquires information about the angle of view θ of the imaging section 200 from the control section 390. The determination section 324 determines whether or not the angle of view θ is smaller than $\theta_{MAX}$.

When the angle of view $\theta = \theta_{MAX}$ (i.e., normal observation state), the determination process that determines whether the state of the object is the stationary state or the moving state is performed using the expression (2) (step S23). When the angle of view $\theta < \theta_{MAX}$ ($\theta \neq \theta_{MAX}$) (i.e., zoom observation state), the determination process that determines whether the state of the object is the stationary state or the moving state is performed using the following expression (3) (step S24).

$$\text{if } mSAD \leq Ca \times N \quad \text{stationary state} \tag{3}$$
$$\text{else} \quad \text{moving state}$$

Ca in the expression (3) is a coefficient that is a real number larger than 1. The coefficient Ca may be a constant value set in advance, or may be an arbitrary value set by the user via the external I/F section 500.

When it has been determined that the state of the object is the stationary state in the step S23 or S24, the time-direction NR process is performed (step S25). When it has been determined that the state of the object is the moving state in the step S23 or S24, the spatial-direction NR process is performed (step S26).

The relationship between the first embodiment and the observation state is described in detail below. An endoscopic examination (diagnosis) is classified into screening that searches for an area that is suspected to be a lesion, and close examination that determines whether or not the area found by screening is a lesion.

Since the doctor performs screening while operating (inserting and withdrawing) the scope, the object moves to a large extent within the image (moving state). Therefore, the time-direction NR process does not function effectively. Since a reddened area or a discolored area is searched for during screening, a component having a relatively low frequency serves as information important for diagnosis. Therefore, diagnosis is affected to only a small extent during screening even if a high-frequency component is attenuated to some extent due to the noise reduction process. Accordingly, it is desirable to reduce noise using the spatial-direction NR process during screening.

On the other hand, since the doctor performs diagnosis during close examination without moving the scope, the object moves to only a small extent within the image (stationary state). A component having a relatively high frequency (e.g., microscopic blood vessel and mucous membrane structure) serves as information important for diagnosis during close examination. Therefore, it is desirable to utilize the time-direction NR process that can maintain a high-frequency component during close examination in which the motion amount is small. Such close examination is normally performed in a zoom observation state.

In the first embodiment, whether the state of the object is the stationary state that corresponds to close examination or the moving state that corresponds to screening are determined with high accuracy, as described above with reference to FIG. 5 and the like. It is possible to reduce only noise during close examination while maintaining a microscopic blood vessel and a mucous membrane structure that are important for diagnosis by selecting the time-direction NR process. The time-direction NR process is more likely to be (dominantly) selected during zoom observation used for close examination by changing the threshold value used for the determination process corresponding to the angle of view θ, as described above with reference to FIG. 10 and the like.

According to the first embodiment, it is possible to adaptively reduce noise from an endoscopic image, and provide an image that is more suitable for diagnosis. Specifically, since the time-direction NR process is likely to be selected when the motion amount is small (e.g., during close examination), it is possible to reduce only noise while maintaining a high-frequency component that is important during close examination.

The spatial-direction NR process is selected during screening. In this case, a high-frequency component of a high-contrast edge area can be maintained, while a high-frequency component of a low-contrast edge area is attenuated. However, diagnosis is affected to only a small extent since a component having a relatively low frequency (e.g., reddened area or discolored area) serves as important information during screening.

2.4. Time-Direction NR Process and Spatial-Direction NR Process

The details of the time-direction NR process are described below. The time-direction NR process is performed using the following expression (4).

$$F_{G\_NR}(x, y) = \frac{we\_cur \times F_{G\_cur}(x, y) + we\_pre \times F_{G\_pre}(x+m, y+n)}{we\_cur + we\_pre} \quad (4)$$

where, $F_{G\_NR}(x, y)$ is the G signal value of the NR image at the coordinates (x, y), and we_cur and we_pre are weighting coefficients used for a weighted averaging process. The noise reduction amount is increased by increasing the weighting coefficient we_pre (as compared with the weighting coefficient we_cur). The weighting coefficients we_cur and we_pre may each be a constant value set in advance, or may each be an arbitrary value set by the user via the external I/F section 500.

The details of the spatial-direction NR process are described below. In the first embodiment, the spatial-direction NR process is a weighted averaging process that utilizes the processing target pixel (attention pixel) and its peripheral pixel. Specifically, noise is reduced using the following expression (5).

$$F_{G\_NR}(x, y) = \quad (5)$$

$$\frac{\sum_{j=-l}^{l}\sum_{i=-l}^{l}\{we\_diff\_cur(x+i, y+j) \times F_{G\_cur}(x+i, y+j)\} + \sum_{j=-l}^{l}\sum_{i=-l}^{l}\{we\_diff\_pre(x+i, y+j) \times F_{G\_pre}(x+i+m, y+j+n)\}}{\sum_{j=-l}^{l}\sum_{i=-l}^{l} we\_diff\_cur(x+i, y+j) + \sum_{j=-l}^{l}\sum_{i=-l}^{l} we\_diff\_pre(x+i, y+j)}$$

where, we_diff_cur(x+i, y+j) and we_diff_pre(x+i, y+j) correspond to weighting coefficients used for the weighted averaging process. The coefficients we_diff_cur(x+i, y+j) and we_diff_pre(x+i, y+j) are given by a Gaussian distribution (see the following expression (6)). l is a natural number, and m and n are m and n of the value SAD(m, n) selected as the average difference value mSAD using the expression (1).

$$we\_diff\_cur(x+i, y+j) = \quad (6)$$
$$\exp\left[-\frac{\{F_{G\_cur}(x+i, y+j) - F_{G\_cur}(x, y)\}^2}{2\sigma^2}\right],$$

$$we\_diff\_pre(x+i, y+j) =$$
$$\exp\left[-\frac{\{F_{G\_pre}(x+i+m, y+j+n) - F_{G\_cur}(x, y)\}^2}{2\sigma^2}\right]$$

In the spatial-direction NR process used in the first embodiment, the weighting coefficient is adaptively set corresponding to the difference between the signal value of the attention pixel and the signal value of the peripheral pixel (see the expression (6)). Specifically, the weight used for the weighted averaging process decreases when the difference is large. Therefore, the pixels of an area (e.g., edge area) in which the signal value suddenly changes do not contribute to the weighted averaging process, and only a noise component can be reduced while maintaining the edge area.

However, since the weighting coefficient is controlled during the spatial-direction NR process corresponding to the difference between the signal value of the attention pixel and the signal value of the peripheral pixel, the degree of noise reduction (i.e., the strength of smoothing) depends on the amount of noise included in the image. Specifically, since the difference increases as the amount of noise increases, the weighting coefficient decreases, and contributes less to the weighted average process (see the expression (5)). Therefore, the degree of noise reduction decreases (i.e., noise is reduced to only a small extent) as the amount of noise increases.

In the first embodiment, the standard deviation σ of the Gaussian distribution (see the expression (6)) is calculated based on the noise amount N output in the step S2 illustrated in FIG. 5 (or the step S21 illustrated in FIG. 10). Specifically, the standard deviation σ is calculated using the following expression (7).

$$\sigma = Cb \times N \quad (7)$$

where, Cb is a coefficient that is a positive real number. The coefficient Cb may be a constant value set in advance, or may be an arbitrary value set by the user via the external I/F section 500.

It is possible to implement a noise reduction process that is adaptive to the noise amount by thus calculating the standard deviation σ of the Gaussian distribution based on the noise amount N. Specifically, since the standard deviation σ increases as the noise amount N increases, the weighting coefficient can be increased as compared with the case where the standard deviation σ does not depend on the noise amount N even when the difference (e.g., $F_{G\_cur}(x+i, y+j) - F_{G\_cur}(x, y)$) (see the expression (6)) has increased due to noise. Therefore, the strength of smoothing can be maintained even when the amount of noise is large.

Although the first embodiment has been described above taking an example in which the NR process is performed on the RGB image output from the interpolation section 310, the first embodiment is not limited thereto. For example, the NR process may be performed on the image output from the image sensor 240. Since the image sensor 240 has a Bayer array, the image output from the image sensor 240 has a configuration in which each pixel has only the R, G, or B signal value. Therefore, the NR process is performed using only the pixels having the R, G, or B signal value. For example, when the attention pixel is a G pixel, the NR process is performed using the attention pixel and its peripheral G pixel.

Although the first embodiment has been described above taking an example in which the signal value of the attention pixel of the RGB image is used as the signal value of the RGB image when acquiring the noise amount N, the first embodiment is not limited thereto. For example, the average value of the attention pixel and its peripheral pixel of the RGB image may be used as the signal value, and the noise amount N corresponding to the signal value may be acquired from the noise amount table.

Although the first embodiment has been described above taking an example in which the estimated noise amount acquisition section 322 acquires the noise amount N from the look-up table 323, the first embodiment is not limited thereto. For example, the estimated noise amount acquisition section 322 may estimate (calculate) the noise amount N based on the RGB image output from the interpolation section 310.

According to the first embodiment, an image processing device includes the evaluation value calculation section 321, the estimated noise amount acquisition section 322, the determination section 324, and the noise reduction processing section 325 (see FIG. 4). The evaluation value calculation section 321 calculates the evaluation value that is used to determine whether or not the inter-frame state of the object (i.e., the state of the object between frames) within the captured image is the stationary state (see the step S1 in FIG. 5). The estimated noise amount acquisition section 322 acquires the estimated noise amount N of the captured image (see the step S2). The determination section 324 determines whether or not the state of the object is the stationary state based on the evaluation value and the estimated noise amount N (see the step S3). The noise reduction processing section 325 performs the first noise reduction process (i.e., time-direction noise reduction process) on the captured image when it has been determined that the state of the object is the stationary state (see the step S4). The noise reduction processing section 325 performs the second noise reduction process that includes at least the spatial-direction noise reduction process on the captured image when it has been determined that the state of the object is not the stationary state (i.e., the state of the object is the moving state) (see the step S5).

More specifically, the determination section 324 uses the estimated noise amount N as a threshold value, and determines that the state of the object is the stationary state when the inter-frame difference value mSAD is equal to or smaller than the threshold value.

The above configuration makes it possible to accurately determine whether or not the state of the object (image) is the stationary state. Specifically, the inter-frame difference value mSAD changes depending on the noise amount (see FIGS. 7A to 8C). According to the first embodiment, since whether or not the inter-frame difference value mSAD corresponds to the stationary state is determined using the estimated noise amount N, it is possible to accurately determine whether or not the state of the object is the stationary state without being affected by the noise amount.

In the first embodiment, the image processing device corresponds to the interpolation section 310, the noise reduction section 320, and the frame memory 330, for example. The captured image corresponds to the RGB image output from the interpolation section 310. The evaluation value corresponds to the inter-frame difference value mSAD. Note that the first embodiment is not limited thereto. It suffices that the evaluation value be a value that is calculated using images in a plurality of frames, and differs between the case where the object is stationary within the image and the case where the object is not stationary within the image.

The time-direction noise reduction process refers to a process that reduces noise of the captured image in the time direction. Specifically, the time-direction noise reduction process refers to a smoothing process performed on time-series pixels, the time-series pixels being the processing target pixel included in the image in the first frame, and the processing target pixel included in the image in the second frame subsequent to the first frame. For example, the processing target pixel included in the image in the first frame is $F_{G\_pre}(x+m, y+n)$, and the processing target pixel included in the image in the second frame is $F_{G\_cur}(x, y)$ (see the expression (4)).

The spatial-direction noise reduction process refers to a process that reduces noise of the captured image in the spatial direction. Specifically, the spatial-direction noise reduction process refers to a smoothing process performed on the processing target pixel included in an image in one frame using the processing target pixel and a pixel around the processing target pixel. For example, the image in one frame is $F_{G\_cur}$, the processing target pixel is (x, y), and the pixel around the processing target pixel is (x+i, y+j) ($-I \leq i \leq I$, $-I \leq j \leq I$) (see the expression (5)).

It suffices that the second noise reduction process that includes at least the spatial-direction noise reduction process include at least the spatial-direction noise reduction process on only the image in one frame. For example, the second noise reduction process may be a noise reduction process that utilizes images in a plurality of frames (see the expression (5)).

An area of the captured image in the first frame $F_{G\_cur}$ that is situated around the processing target pixel (x, y) and has a given size ($(2k+1)^2$ pixels) may be referred to as a first area, and an area of the captured image in the second frame $F_{G\_pre}$ that is situated around the processing target pixel (x, y) and has a given size ($(2k+1)^2$ pixels) may be referred to as a second area (see the expression (1)). In this case, the evaluation value calculation section 321 may calculate a plurality of difference values SAD(m, n) between the pixel value of the first area and the pixel value of the second area while sequentially shifting (m and n=−1, 0, 1) the second area by one pixel relative to the first area in the horizontal direction (i.e., the direction along the x-axis) and the vertical direction (i.e., the direction along the y-axis). The evaluation value calculation section 321 may output a minimum value min(SAD(m, n)) among the plurality of difference values SAD(m, n) as the inter-frame difference value mSAD. The determination section 324 may determine that the state of the object is the stationary state when the minimum value is equal to or smaller than the threshold value N.

According to the above configuration, the time-direction NR process can be selected even when the object moves by about 1 pixel between the frames. Specifically, since the object is not necessarily completely stationary within the image even in the stationary state, the time-direction NR process is selected when the motion of the object is within a range that is considered to be the stationary state to implement the noise reduction process while maintaining the structural information.

The image processing device may include the angle-of-view information acquisition section 326 that acquires the angle-of-view information about the imaging section 200 that captures the captured image (see FIG. 4). The determination section 324 may set a determination condition for determining whether or not the state of the object is the stationary state corresponding to the angle of view θ indicated by the angle-of-view information.

More specifically, the evaluation value calculation section 321 may calculate the inter-frame difference value mSAD of the captured image as the evaluation value (see the step S20 in FIG. 10). The determination section 324 may determine that the state of the object is the stationary state when the angle of view θ is equal to or larger than the threshold value $\theta_{MAX}$, and the inter-frame difference value mSAD is equal to or smaller than the estimated noise amount N (see the steps S22 and S23). The determination section 324 may determine that the state of the object is the stationary state when the angle of view θ is smaller than the threshold value $\theta_{MAX}$, and the inter-frame difference value mSAD is equal to or smaller than a value obtained by multiplying the estimated noise amount N by the coefficient Ca that is larger than 1 (see the steps S22 and S24).

Although the first embodiment has been described above taking an example in which the upper limit $\theta_{MAX}$ of the angle-of-view adjustment range $\theta_{MIN}$ to $\theta_{MAX}$ is used as the angle-of-view determination threshold value, the first embodiment is not limited thereto. For example, a given angle of view within the angle-of-view adjustment range $\theta_{MIN}$ to $\theta_{MAX}$ may be used as the threshold value.

According to the above configuration, the observation state can be determined to be the zoom observation state when the angle of view θ of the imaging section 200 is smaller than the threshold value. When the observation state has been determined to be the zoom observation state, the time-direction NR process is more likely to be selected as compared with the normal observation state by setting the threshold value to the value CaN that is larger than the estimated noise amount N. This makes it possible to improve the visibility of a microscopic structure (e.g., lesion area) in the zoom observation state.

3. Second Embodiment

3.1. Endoscope System

A second embodiment in which the determination process that determines whether the state of the object is the stationary state or the moving state is performed using a threshold value that differs between the front field of view and the side field of view of the imaging section 200 is described below.

Figure 11:
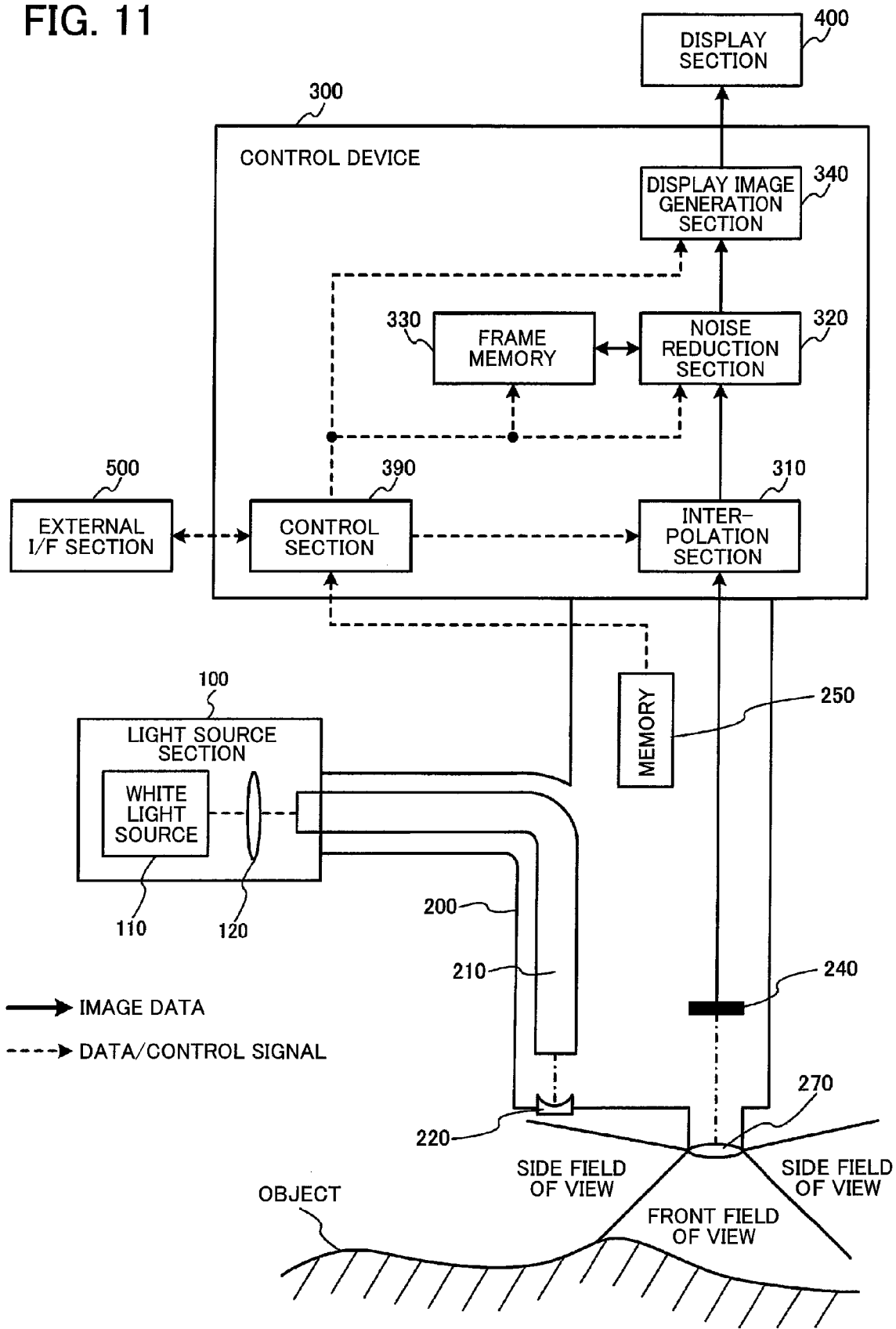
FIG. 11 illustrates a configuration example of an endoscope system according to a second embodiment.

FIG. 11 illustrates a configuration example of an endoscope system according to the second embodiment. The endoscope system includes a light source section 100, an imaging section 200, a control device 300, a display section 400, and an external I/F section 500. Note that the same elements as those of the endoscope system according to the first embodiment are respectively indicated by the same reference signs, and description thereof is appropriately omitted. The elements other than the imaging section 200 and the control device 300 are the same as those described above in connection with the first embodiment, and description thereof is omitted.

The imaging section 200 includes a light guide fiber 210, an illumination lens 220, a condenser lens 270, an image sensor 240, and a memory 250. The light guide fiber 210, the illumination lens 220, the image sensor 240, and the memory 250 are the same as those described above in connection with the first embodiment, and description thereof is omitted. The condenser lens 270 protrudes from the end of the imaging section 200 so that the front field of view and the side field of view can be observed. The condenser lens 270 is implemented by an objective lens having a viewing angle of 230°, for example.

Figure 12:
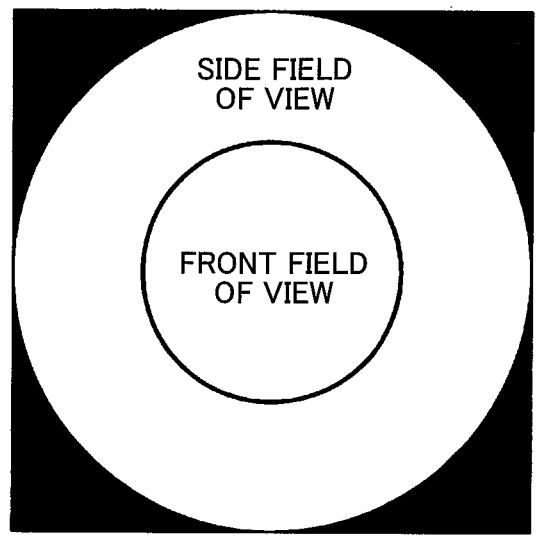
FIG. 12 is a view illustrating a front-field-of-view area and a side-field-of-view area.
Figure 13:
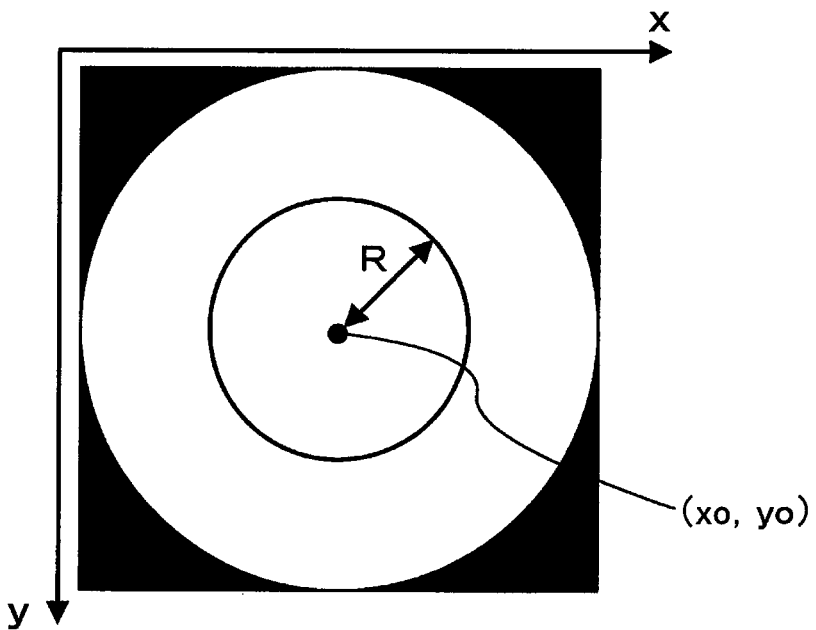
FIG. 13 is a view illustrating an area determination process.

The interpolation section 310 outputs an RGB image that includes a front-field-of-view area in which the object within the front field of view is captured, and a side-field-of-view area in which the object within the side field of view is captured (see FIG. 12). The center area of the RGB image corresponds to the front field of view, and the peripheral area of the RGB image corresponds to the side field of view. As illustrated in FIG. 13, the center coordinates of the RGB image are indicated by (xo, yo). An area situated within the range of a radius R around the center coordinates (xo, yo) is the front-field-of-view area, and an area situated outside the range of the radius R is the side-field-of-view area.

The control device 300 includes an interpolation section 310, a noise reduction section 320, a frame memory 330, a display image generation section 340, and a control section 390. The process performed by each element other than the noise reduction section 320 is the same as those described above in connection with the first embodiment, and description thereof is omitted.

3.2. Noise Reduction Process

Figure 14:
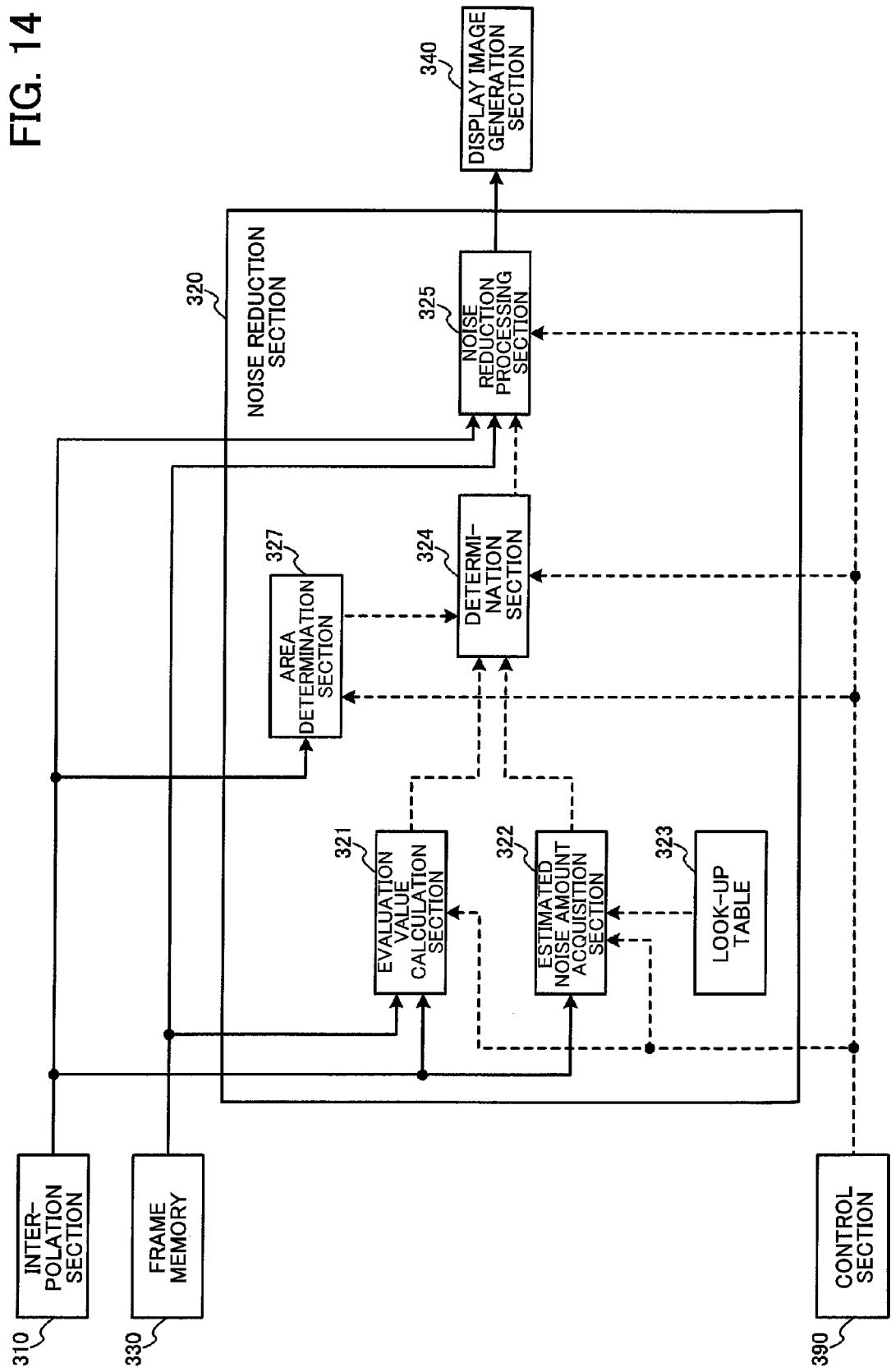
FIG. 14 illustrates a detailed configuration example of a noise reduction section according to the second embodiment.

FIG. 14 illustrates a detailed configuration example of the noise reduction section 320 according to the second embodiment. The noise reduction section 320 includes an evaluation value calculation section 321, an estimated noise amount acquisition section 322, a look-up table 323, a determination section 324, a noise reduction processing section 325, and an area determination section 327.

Figure 15:
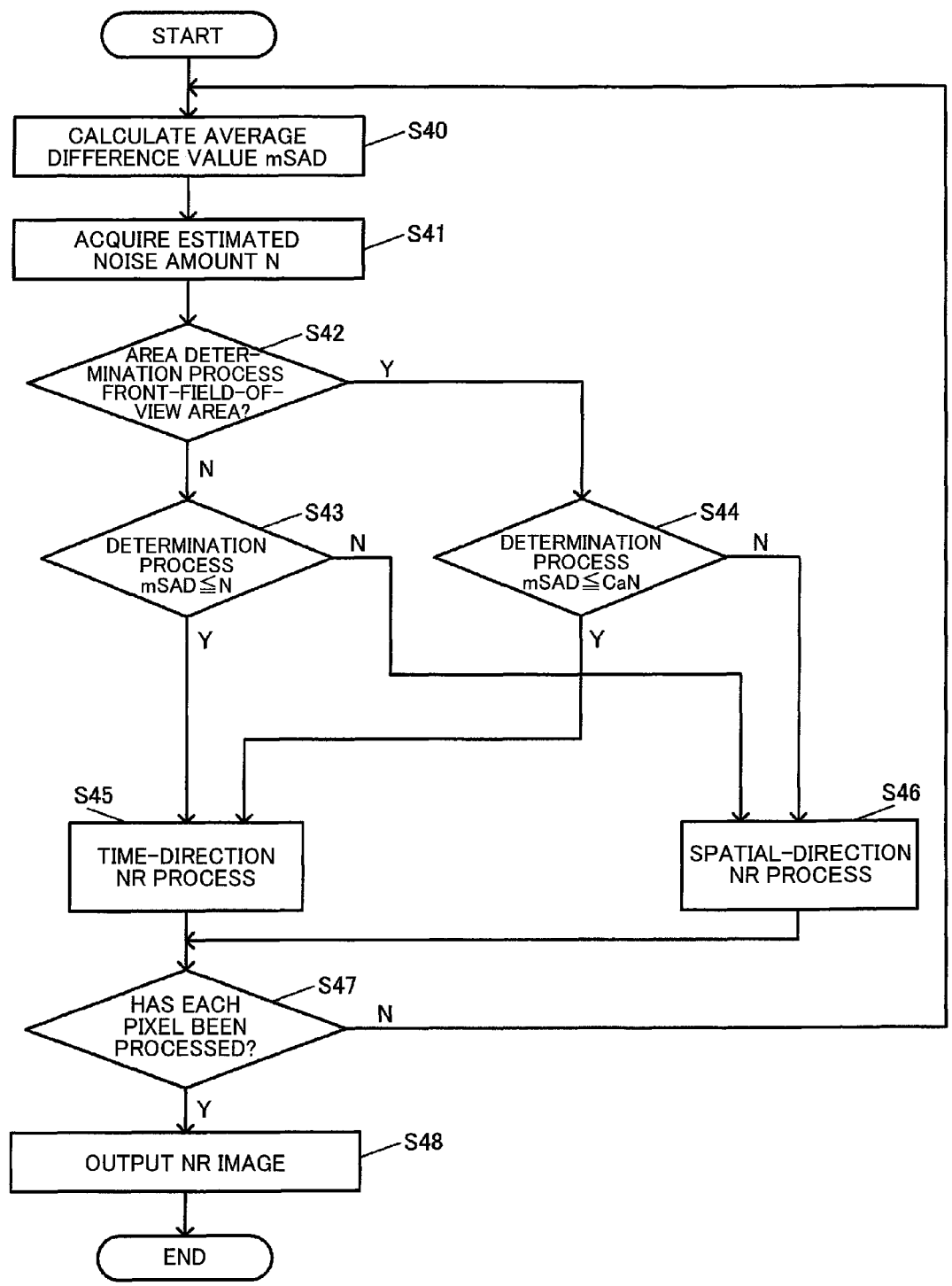
FIG. 15 is a flowchart illustrating a noise reduction process according to the second embodiment.

FIG. 15 is a flowchart illustrating the noise reduction process according to the second embodiment. Note that the steps other than a step S42 are the same as those described above with reference to FIG. 5 or 10, and description thereof is appropriately omitted.

In the step S42, the area determination section 327 performs a determination process that determines an area to which the attention pixel belongs. Specifically, the area determination section 327 determines whether the attention pixel belongs to the front-field-of-view area or the side-field-of-view area using the following expression (8). Note that r in the expression (8) is calculated by the following expression (9). (x, y) in the expression (9) are the coordinates of the attention pixel.

$$\text{if } r \leq R \quad \text{front field of view} \quad (8)$$
$$\text{else} \quad \text{side field of view}$$

$$r = \sqrt{(x - xo)^2 + (y - yo)^2} \quad (9)$$

In steps S43 and S44, the determination section 324 performs the determination process based on the average difference value mSAD output in a step S40, the noise amount N output in a step S41, and information (about the area to which the attention pixel belongs) output in the step S42. Specifically, when it has been determined that the attention pixel belong to the side-field-of-view area, the determination section 324 determine whether or not the state of the object is the stationary state using the expression (2) (step S44). When it has been determined that the attention pixel belong to the front-field-of-view area, the determination section 324 determine whether or not the state of the object is the stationary state using the expression (3) (step S43).

An image acquired using a lens having a wide viewing angle is normally distorted to a large extent in the peripheral area, and a high-frequency component in the peripheral area is lost. Therefore, the side-field-of-view area of the image acquired according to the second embodiment is suitable for screening, but is not suitable for close examination as compared with the front-field-of-view area that is distorted to only a small extent.

In the second embodiment, the determination process is performed while setting the threshold value used for the front-field-of-view area to be larger than the threshold value used for the side-field-of-view area. This makes it possible to predominantly use the spatial-direction NR process for the side-field-of-view area, and predominantly use the time-direction NR process for the front-field-of-view area, so that an adaptive NR process can be implemented. Specifically, the time-direction NR process is made likely to be selected for the front-field-of-view area that is considered to be used for close examination by setting the threshold value to CaN (Ca>1) to reduce only noise while maintaining a high-frequency component. On the other hand, the spatial-direction NR process is made likely to be selected for the side-field-of-view area that is considered to be used for screening by setting the threshold value to N to suppress a residual image. This makes it possible to present an image that is more suitable for diagnosis to the doctor.

According to the second embodiment, the determination section 324 sets the determination condition for determining whether or not the state of the object is the stationary state corresponding to an area of the captured image to which the target area of the noise reduction process belongs.

The above configuration makes it possible allow the time-direction NR process to be more likely to be selected for an area used for observation of a microscopic structure. This makes it possible to improve the visibility of a microscopic structure (e.g., lesion area) within the area.

Specifically, the image processing device may include the area determination section 327 (see FIG. 14). As described above with reference to FIGS. 11 and 12, the imaging section 200 may be able to capture the front field of view and the side field of view of the imaging section 200. As described above with reference to FIG. 13, the area determination section 327 may determine whether the target area belongs to the front-field-of-view area of the captured image or the side-field-of-view area of the captured image, the front-field-of-view area being an area that corresponds to the front field of view, and the side-field-of-view area being an area that corresponds to the side field of view. The determination section 324 may set the determination condition that differs between the case where it has been determined that the target area belongs to the front-field-of-view area and the case where it has been determined that the target area belongs to the side-field-of-view area.

More specifically, the determination section 324 may determine that the state of the object is the stationary state when it has been determined that the target area belongs to the side-field-of-view area, and the inter-frame difference value mSAD is equal to or smaller than the estimated noise amount N (see the steps S42 and S43 in FIG. 15). The determination section 324 may determine that the state of the object is the stationary state when it has been determined that the target area belongs to the front-field-of-view area, and the inter-frame difference value mSAD is equal to or smaller than a value obtained by multiplying the estimated noise amount N by the coefficient Ca that is larger than 1 (see the steps S42 and S44).

For example, the area determination section 327 may determine an area to which the target area belongs based on the position (x, y) of the target area within the captured image, as described with reference to FIG. 13.

According to the above configuration, when it has been determined that the target area belongs to the front-field-of-view area, the time-direction NR process is more likely to be selected as compared with the side-field-of-view area by setting the threshold value to the value CaN that is larger than the estimated noise amount N.

The target area of the noise reduction process may include only one pixel, or may include a plurality of pixels. For example, when performing the first noise reduction process (see the expression (4)) or the second noise reduction process (see the expression (5)), the pixel (x, y) is the target area.

The front field of view refers to a field-of-view range that includes the optical axis direction of the imaging section 200 (e.g., the range of 0 to 70° with respect to the optical axis). The side field of view refers to a field-of-view range that includes the direction orthogonal to the optical axis. For example, when the field-of-view range of the imaging section 200 is the range of 0 to 115° with respect to the optical axis, the side field of view is the range of 70 to 115° with respect to the optical axis.

4. Third Embodiment

4.1. Endoscope System

A third embodiment in which the determination process that determines whether the state of the object is the stationary state or the moving state is performed using a threshold value that differs between a white light image and a special light image is described below.

Figure 16:
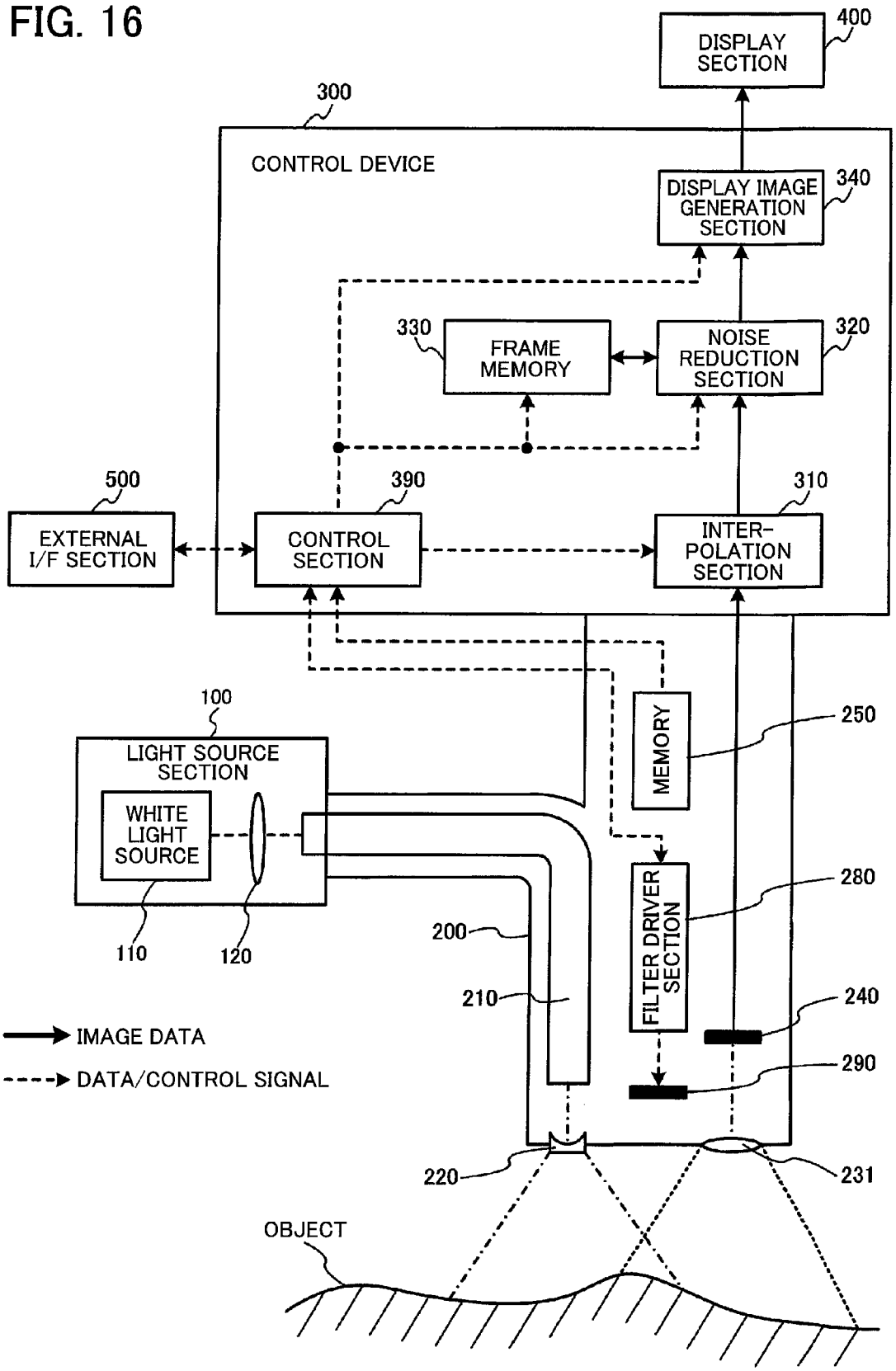
FIG. 16 illustrates a configuration example of an endoscope system according to a third embodiment.

FIG. 16 illustrates a configuration example of an endoscope system according to the third embodiment. The endoscope system includes a light source section 100, an imaging section 200, a control device 300, a display section 400, and an external I/F section 500. Note that the same elements as those of the endoscope system according to the first embodiment are respectively indicated by the same reference signs, and description thereof is appropriately omitted. The elements other than the imaging section 200 and the control device 300 are the same as those described above in connection with the first embodiment, and description thereof is omitted.

The imaging section 200 includes a light guide fiber 210, an illumination lens 220, a condenser lens 290, an image sensor 240, a memory 250, a narrow-band filter 290, and a filter driver section 280. The light guide fiber 210, the illumination lens 220, the image sensor 240, and the memory 250 are the same as those described above in connection with the first embodiment, and description thereof is omitted. The filter driver section 280 is connected to the narrow-band filter 290, and is bidirectionally connected to the control section 390.

Figure 17:
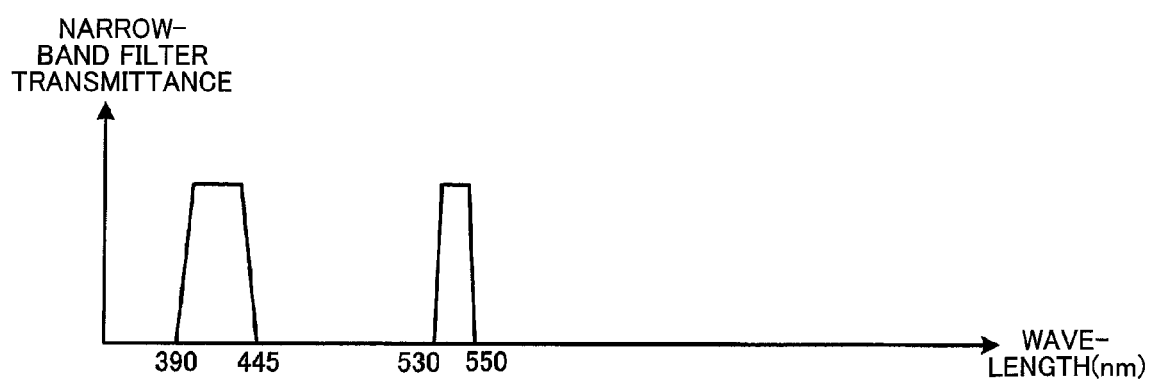
FIG. 17 illustrates an example of the transmittance characteristics of a narrow-band filter.

As illustrated in FIG. 17, the narrow-band filter 290 allows light having a wavelength of 380 to 450 nm and light having a wavelength of 530 to 550 nm to pass through. The narrow-band filter 290 can be inserted into the optical path between the condenser lens 231 and the image sensor 240. The user controls insertion of the narrow-band filter 290 via the external I/F section 500, for example. In this case, an instruction issued by the user is transmitted to the filter driver section 280 from the external I/F section 500 through the control section 390, and the filter driver section 280 drives the narrow-band filter 290. When the narrow-band filter 290 is inserted into the optical path, the control section 390 outputs a trigger signal to the interpolation section 310 and the noise reduction section 320.

The control device 300 includes an interpolation section 310, a noise reduction section 320, a frame memory 330, a display image generation section 340, and a control section 390.

The interpolation section 310 performs an interpolation process on the image acquired by the image sensor 240. The interpolation section 310 generates an RGB image in the same manner as described above in connection the first embodiment when the trigger signal is not output from the control section 390 (i.e., when the narrow-band filter 290 is not inserted into the optical path). An RGB image acquired when the narrow-band filter 290 is not inserted into the optical path is hereinafter referred to as "white light image (normal light image in a broad sense)".

The interpolation section 310 performs the interpolation process on only the G signal and the B signal when the trigger signal is output from the control section 390 (i.e., when the narrow-band filter 290 is inserted into the optical path). A known bicubic interpolation process may be used as the interpolation process, for example. In this case, the interpolation section 310 generates a G image in which each pixel has a G signal, and a B image in which each pixel has a B signal by performing the interpolation process. The G image is input to the R signal of an RGB image, and the B image is input to the G signal and the B signal of an RGB image to generate an RGB image. An RGB image acquired when the narrow-band filter 290 is inserted into the optical path is hereinafter referred to as "narrow-band light image (special light image in a broad sense)".

4.2. Noise Reduction Process

Figure 18:
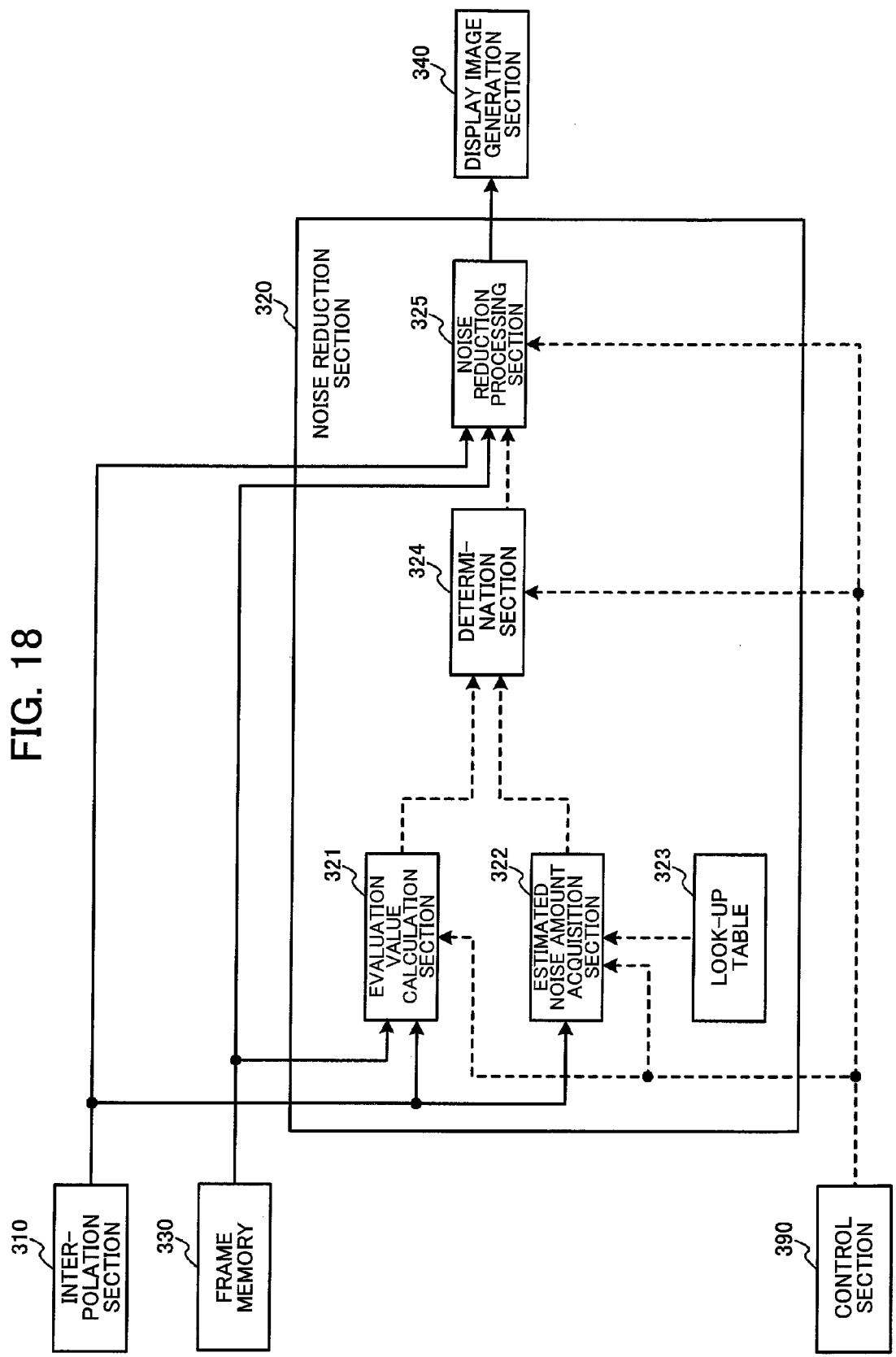
FIG. 18 illustrates a detailed configuration example of a noise reduction section according to the third embodiment.

FIG. 18 illustrates a detailed configuration example of the noise reduction section 320 according to the third embodiment. The noise reduction section 320 includes an evaluation value calculation section 321, an estimated noise amount acquisition section 322, a look-up table 323, a determination section 324, and a noise reduction processing section 325.

Figure 19:
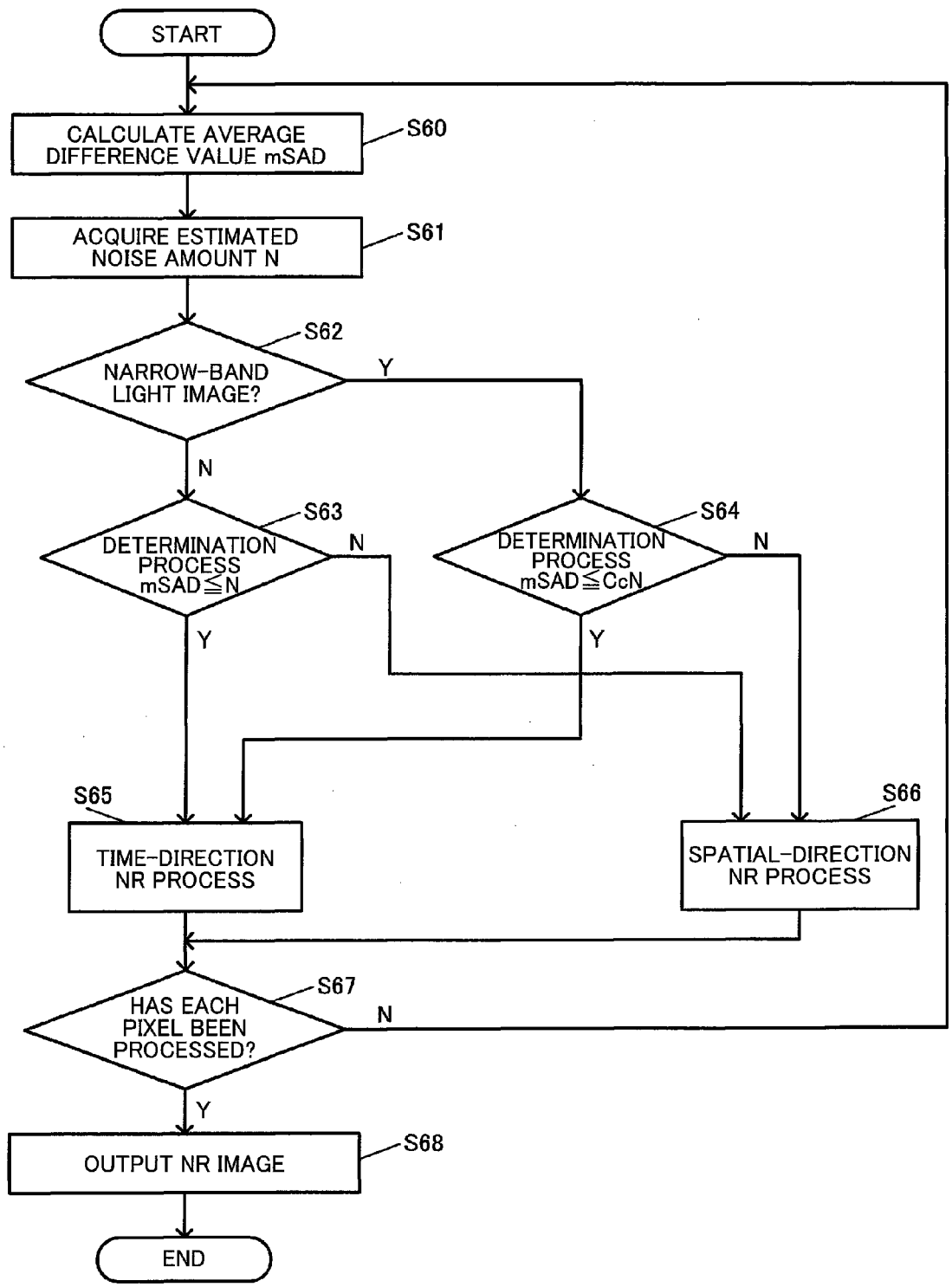
FIG. 19 is a flowchart illustrating a noise reduction process according to the third embodiment.

FIG. 19 is a flowchart illustrating the noise reduction process according to the third embodiment. Note that the steps other than steps S62 and S64 are the same as those described above with reference to FIG. 5 or 10, and description thereof is appropriately omitted.

In the steps S62 to S64, the determination section 324 performs the determination process based on the average difference value mSAD output in a step S60, the noise amount N output in a step S61, and the trigger signal output from the control section 390. Specifically, the determination section 324 performs the determination process using the following expression (10) when the trigger signal is output from the control section 390. Note that Cc in the expression (10) is a coefficient that is a real number smaller than 1. The determination section 324 performs the determination process using the expression (2) when the trigger signal is not output from the control section 390.

$$\text{if } mSAD \le Cc \times N \quad \text{stationary state} \qquad (10)$$
$$\text{else} \qquad \text{moving state}$$

The narrow-band light image normally includes a large amount of noise (i.e., has a low S/N ratio) as compared with the white light image due to insufficient intensity of light. Therefore, the structural component described above with reference to FIG. 6A is embedded in the noise component described above with reference to FIG. 6B, and the accuracy of the stationary state/moving state determination process deteriorates. Specifically, the state of the object may be determined to be the stationary state although the state of the object is the moving state, and the time-direction NR process may be selected. In this case, a residual image may occur due to the time-direction NR process.

According to the third embodiment, the determination process that determines whether or not the state of the object is the stationary state is performed using the expression (10) when the narrow-band light image is acquired. The threshold value decreases as compared with the case where the image is the white light image since Cc<1, and the spatial-direction NR process is predominantly performed. This makes it possible to reduce the possibility that the state of the object is determined to be the stationary state although the state of the object is the moving state, and suppress occurrence of a residual image. It is possible to implement an adaptive NR process by thus controlling the threshold value used for the motion determination process corresponding to the observation mode (white light image observation or narrow-band light image observation) of the endoscope.

According to the third embodiment, the determination section 324 sets the determination condition for determining whether or not the state of the object is the stationary state corresponding to the type of the captured image.

According to the above configuration, the first noise reduction process or the second noise reduction process is likely to be selected corresponding to the characteristics of the captured image. For example, it is possible to improve the visibility of a microscopic structure, or suppress a situation in which the state of the object is erroneously determined to be the stationary state.

Note that the type of the captured image is determined by the number of pixels of the captured image, the resolution, the exposure time, the frame rate, the type of the connected imaging section 200, the characteristics of the illumination light, the characteristics of an optical filter used for imaging, and the like.

As described above with reference to FIG. 16, the captured image may be a white light image that includes information within the white wavelength band, or a special light image (narrow-band light image in a narrow sense) that includes information within a specific wavelength band. The determination section 324 may set the determination condition that differs between the case where the captured image is the white light image and the case where the captured image is the special light image.

More specifically, the determination section 324 may determine that the state of the object is the stationary state when the captured image is the white light image, and the inter-frame difference value mSAD is equal to or smaller than the estimated noise amount N (see the steps S62 and S63 in FIG. 19). The determination section 324 may determine that the state of the object is the stationary state when the captured image is the special light image, and the inter-frame difference value mSAD is equal to or smaller than a value obtained by multiplying the estimated noise amount N by the coefficient Cc that is smaller than 1 (see the steps S62 and S64).

According to the above configuration, when it has been determined that the captured image is the special light image, the second noise reduction process that includes at least the spatial-direction noise reduction process is more likely to be selected as compared with the case where the captured image is the white light image by setting the threshold value to the value CcN that is smaller than the estimated noise amount N. This makes it possible to suppress a situation in which the state of the object is erroneously determined to be the stationary state when the captured image is the special light image of which the S/N ratio is lower than that of the white light image.

Although the third embodiment has been described above taking an example in which the special light image is captured by inserting the narrow-band filter 290 into the optical path, the third embodiment is not limited thereto. For example, the special light image may be captured by causing the light source section 100 to emit special light (narrow-band light in a narrow sense). Alternatively, the imaging section 200 may further include an image sensor having a color filter that allows special light to pass through, and may capture the special light image using the image sensor. Alternatively, the special light image may be generated from the white light image by image processing.

In the third embodiment, the specific wavelength band may be a band that is narrower than the wavelength band (e.g., 380 to 650 nm) of white light (i.e., narrow-band imaging (NBI)). The normal light image and the special light image may each be an in vivo image, and the specific wavelength band included in the in vivo image may be the wavelength band of light absorbed by hemoglobin in blood, for example. The wavelength band of light absorbed by hemoglobin may be 390 to 445 nm (first narrow-band light or the B2 component of narrow-band light) or 530 to 550 nm (second narrow-band light or the G2 component of narrow-band light), for example.

The above configuration makes it possible to observe the structure of a surface area of tissue and a blood vessel situated in a deep area. A lesion area (e.g., epidermoid cancer) that is difficult to observe using normal light can be displayed in brown or the like by inputting the resulting signal to a specific channel (G2→R, B2→G and B), so that the lesion area can be reliably detected. A wavelength band of 390 to 445 nm or 530 to 550 nm is selected from the viewpoint of absorption by hemoglobin and the ability to reach a surface area or a deep area of tissue. Note that the wavelength band is not limited thereto. For example, the lower limit of the wavelength band may decrease by about 0 to 10%, and the upper limit of the wavelength band may increase by about 0 to 10%, depending on a variation factor (e.g., experimental results for absorption by hemoglobin and the ability to reach a surface area or a deep area of tissue).

5. Fourth Embodiment

5.1. Endoscope System

A fourth embodiment in which the inter-frame motion vector of the object is detected, and the determination process that determines whether the state of the object is the stationary state or the moving state is performed between frames that are shifted in position by the motion vector is described below.

Figure 20:
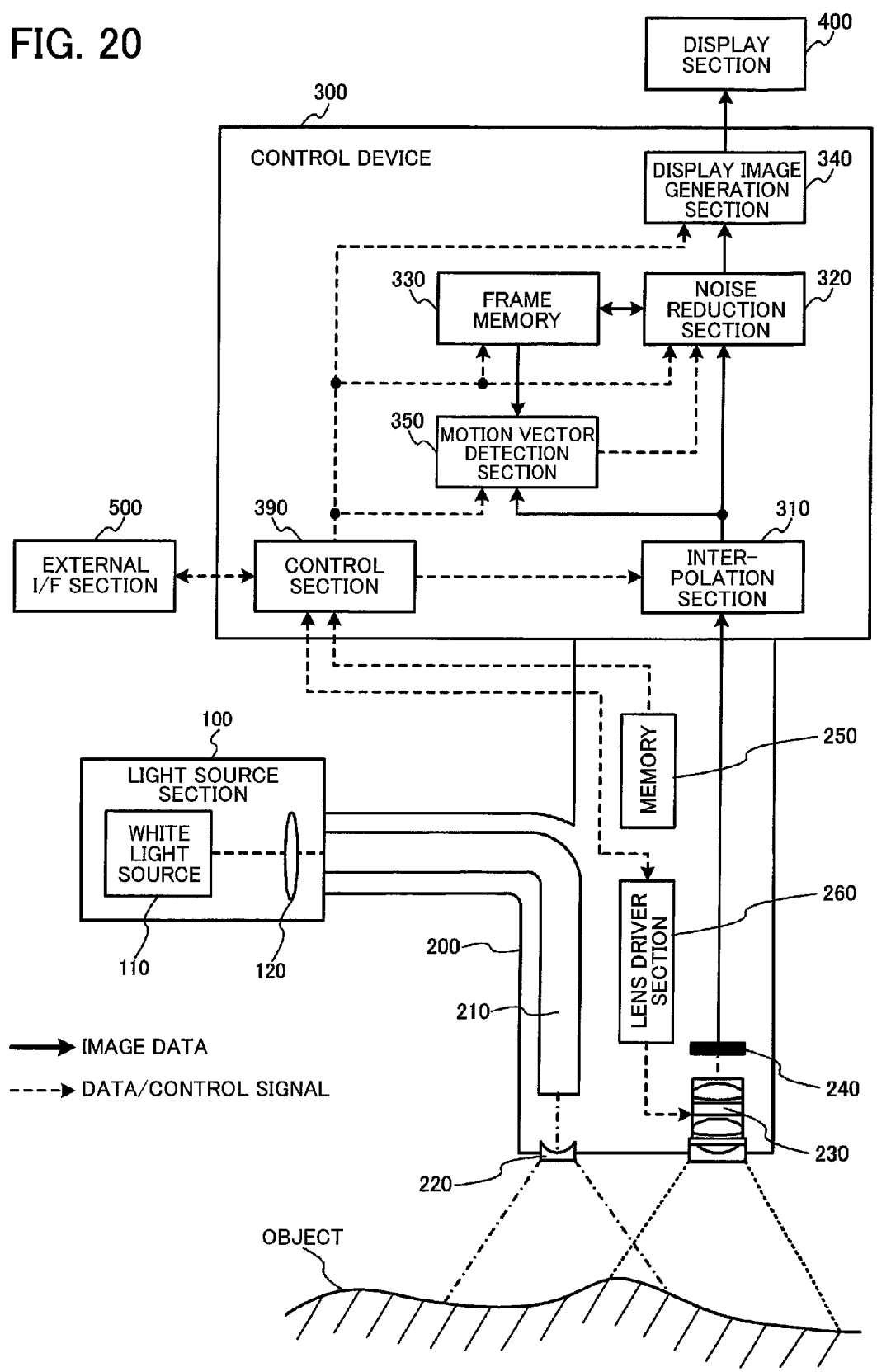
FIG. 20 illustrates a configuration example of an endoscope system according to a fourth embodiment.

FIG. 20 illustrates a configuration example of an endoscope system according to the fourth embodiment. The endoscope system includes a light source section 100, an imaging section 200, a control device 300, a display section 400, and an external I/F section 500. Note that the same elements as those of the endoscope system according to the first embodiment are respectively indicated by the same reference signs, and description thereof is appropriately omitted. The elements other than the control device 300 are the same as those described above in connection with the first embodiment, and description thereof is omitted.

The control device 300 includes an interpolation section 310, a noise reduction section 320, a frame memory 330, a display image generation section 340, a motion vector detection section 350, and a control section 390. The configuration of the control device 300 is the same as that described above in connection with the first embodiment, except that the motion vector detection section 350 is additionally provided.

The motion vector detection section 350 detects a motion vector (Vec_x, Vec_y) based on the RGB image output from the interpolation section 310 and the preceding image stored in the frame memory 330. The motion vector may be detected using a known block matching process, for example. The motion vector is calculated for each pixel, for example.

5.2. Noise Reduction Process

Figure 21:
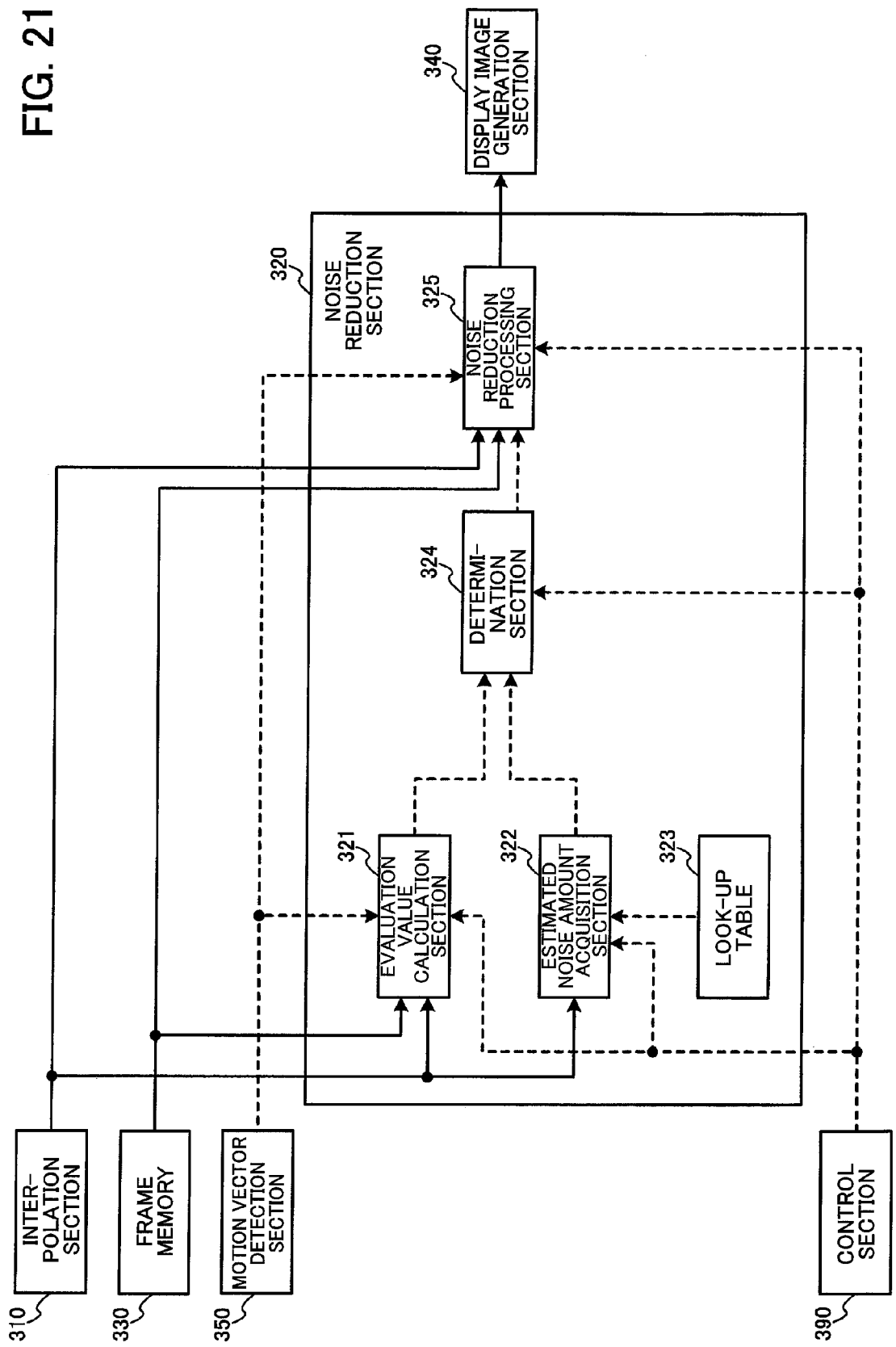
FIG. 21 illustrates a detailed configuration example of a noise reduction section according to the fourth embodiment.

FIG. 21 illustrates a detailed configuration example of the noise reduction section 320 according to the fourth embodiment. The noise reduction section 320 includes an evaluation value calculation section 321, an estimated noise amount acquisition section 322, a look-up table 323, a determination section 324, and a noise reduction processing section 325.

The flowchart illustrated in FIG. 10 described above in connection with the first embodiment is applied to the noise reduction process according to the fourth embodiment. The steps other than the steps S20, S25, and S26 are the same as those described above in connection with the first embodiment, and description thereof is appropriately omitted.

In the step S20, the evaluation value calculation section 321 calculates the average difference value mSAD using the following expression (11). Specifically, the motion vector detection section 350 detects the motion vector (Vec_x, Vec_y), and the evaluation value calculation section 321 calculates the average difference value mSAD taking account of the motion vector (Vec_x, Vec_y).

$$mSAD = \min \begin{Bmatrix} SAD(-1,-1), & SAD(0,-1), & SAD(1,-1) \\ SAD(-1,0), & SAD(0,0), & SAD(1,0), \\ SAD(-1,1), & SAD(0,1), & SAD(1,1), \end{Bmatrix} \quad (11)$$

$$SAD(m,n) = \frac{1}{(2k+1)^2} \sum_{j=-k}^{k} \sum_{i=-k}^{k} \|F_{G\_cur}(x+i, y+j) - F_{G\_pre}(x+i+\text{Vec}\_x+m, y+j+\text{Vec}\_y+n)\|$$

In the step S25, the noise reduction processing section 325 performs the time-direction NR process taking account of the motion vector (Vec_x, Vec_y) (see the following expression (12)).

$$F_{G\_NR}(x, y) = \frac{we\_cur \times F_{G\_cur}(x, y) + we\_pre \times F_{G\_pre}(x + vec\_x + m, y + vec\_y + n)}{we\_cur + we\_pre} \quad (12)$$

In the step S26, the noise reduction processing section 325 performs the spatial-direction NR process taking account of the motion vector (Vec_x, Vec_y) (see the following expression (13)).

$$F_{G\_NR}(x, y) = \quad (13)$$

$$\frac{\sum_{j=-l}^{l}\sum_{i=-l}^{l}\{we\_diff\_cur(x+i, y+j) \times F_{G\_cur}(x+i, y+j)\} + \sum_{j=-l}^{l}\sum_{i=-l}^{l}\left\{\begin{array}{l}we\_diff\_pre(x+i, y+j) \times \\ F_{G\_pre}(x+i+vec\_x+m, y+j+vec\_y+n)\end{array}\right\}}{\sum_{j=-l}^{l}\sum_{i=-l}^{l}we\_diff\_cur(x+i, y+j) + \sum_{j=-l}^{l}\sum_{i=-l}^{l}we\_diff\_pre(x+i, y+j)}$$

The weighting coefficients we_cur and we_pre in the expression (13) are given by the following expression (14).

$$we\_diff\_cur(x+i, y+j) = \quad (14)$$

$$\exp\left[-\frac{\{F_{G\_cur}(x+i, y+j) - F_{G\_cur}(x, y)\}^2}{2\sigma^2}\right],$$

$$we\_diff\_pre(x+i, y+j) =$$

$$\exp\left[-\frac{\left\{F_{G\_pre}\left(\begin{array}{l}x+i+vec\_x+m, \\ y+j+vec\_y+n\end{array}\right) - F_{G\_cur}(x, y)\right\}^2}{2\sigma^2}\right]$$

According to the fourth embodiment, the time-direction NR process functions effectively even when the motion amount is large (e.g., during screening) by taking account of the motion vector. Specifically, since the pixel position of the preceding image $F_{G\_pre}$ is subjected to motion compensation in the expression (11), the state of the object is determined to be the stationary state when the motion vector detection process can follow the motion of the object, and the time-direction NR process is selected. This makes it possible to attenuate only noise while maintaining a high-frequency component even when the object makes a motion.

According to the fourth embodiment, the image processing device includes the motion vector detection section 350 that detects the motion vector (Vec_x, Vec_y) of the object within the captured image between the first frame and the second frame (see FIG. 20). The evaluation value calculation section 321 calculates the evaluation value (inter-frame difference value mSAD) that is used to determine whether or not the state of the object is the stationary state between the first frame and the second frame that is subjected to motion compensation using the motion vector (Vec_x, Vec_y) (see the expression (11)). The noise reduction processing section 325 performs the first noise reduction process and the second noise reduction process based on the first frame and the second frame that is subjected to motion compensation using the motion vector (Vec_x, Vec_y) (see the expressions (12) to (14)).

Note that the expression "subjected to motion compensation using the motion vector" used herein means that the pixel position of the second frame is compensated using the motion vector during the determination process or the noise reduction process. For example, the pixel position of the second frame $F_{G\_pre}$ in the expression (11) is shifted relative to the pixel position of the first frame $F_{G\_cur}$ by the motion vector (Vec_x, Vec_y).

Note that part or the entirety of the process performed by the image processing device and the like described above in connection with the first to fourth embodiments may be implemented by a program. In this case, the image processing device and the like are implemented by causing a processor (e.g., CPU) to execute the program. Specifically, a program stored in an information storage medium (device) is read from the information storage medium, and a processor (e.g., CPU) executes the program read from the information storage medium. The information storage medium (computer-readable medium) stores a program, data, and the like. The function of the information storage medium may be implemented by an optical disk (e.g., DVD or CD), a hard disk drive (HDD), a memory (e.g., memory card or ROM), or the like. The processor (e.g., CPU) performs various processes according to the embodiments of the invention based on a program (data) stored in the information storage medium. Specifically, a program that causes a computer (i.e., a device including an operation section, a processing section, a storage section, and an output section) to function as each section according to the embodiments of the invention (i.e., a program that causes a computer to execute the process implemented by each section) is stored in the information storage medium.

The embodiments of the invention and the modifications thereof have been described above. Note that the invention is not limited to the above embodiments and modifications thereof. Various modifications and variations may be made without departing from the scope of the invention. A plurality of elements described in connection with the above embodiments and the modifications thereof may be appropriately combined to implement various configurations. For example, some of the elements described in connection with the above embodiments and the modifications thereof may be omitted. The elements described above in connection with different embodiments and modifications thereof may be appropriately combined. Specifically, various modifications and applications are possible without materially departing from the novel teachings and advantages of the invention. The application of the embodiments of the invention is not limited to an endoscope system. The embodiments of the invention may also be applied to various imaging systems such as a digital video camera.

Any term cited with a different term having a broader meaning or the same meaning at least once in the specification and the drawings can be replaced by the different term in any place in the specification and the drawings.

What is claimed is:
1. An image processing device comprising:
an evaluation value calculation section that calculates an evaluation value that is used to determine whether or not an inter-frame state of an object within a captured image is a stationary state;
an estimated noise amount acquisition section that acquires an estimated noise amount of the captured image;
a determination section that determines whether or not the inter-frame state of the object is the stationary state based on the evaluation value, the estimated noise amount, and a specific condition; and a noise reduction processing section that performs a first noise reduction process that is a time-direction noise reduction process on the captured image when it has been determined that the inter-frame state of the object is the stationary state, and performs a second noise reduction process that includes at least a spatial-direction noise reduction process on the captured image when it has been determined that the inter-frame state of the object is not the stationary state, wherein the determination section uses, as the specific condition, one of (i) angle-of-view information about an imaging section that captures the captured image, (ii) whether a target area of a noise reduction process belongs to a front-field-of-view area or a side-field-of-view area, and (iii) whether a type of the captured image belongs to a white light image or a special light image.

2. The image processing device as defined in claim 1, further comprising:

an angle-of-view information acquisition section that acquires the angle-of-view information about the imaging section that captures the captured image, wherein the determination section sets a determination condition for determining whether or not the inter-frame state of the object is the stationary state corresponding to an angle of view indicated by the angle-of-view information.

3. The image processing device as defined in claim 2, wherein:

the evaluation value calculation section calculates an inter-frame difference value of the captured image as the evaluation value, and the determination section determines that the inter-frame state of the object is the stationary state when the angle of view is equal to or larger than a threshold value, and the inter-frame difference value is equal to or smaller than the estimated noise amount, and the determination section also determines that the inter-frame state of the object is the stationary state when the angle of view is smaller than the threshold value, and the inter-frame difference value is equal to or smaller than a value obtained by multiplying the estimated noise amount by a coefficient that is larger than 1.

4. The image processing device as defined in claim 1, wherein the determination section sets a determination condition for determining whether or not the inter-frame state of the object is the stationary state corresponding to an area of the captured image to which the target area of the noise reduction process belongs.

5. The image processing device as defined in claim 4, further comprising:

an area determination section, and the imaging section that captures the captured image, wherein the imaging section is capable of capturing a front field of view and a side field of view of the imaging section, wherein the area determination section determines whether the target area belongs to the front-field-of-view area of the captured image or the side-field-of-view area of the captured image, the front-field-of-view area being an area that corresponds to the front field of view, and the side-field-of-view area being an area that corresponds to the side field of view, and the determination section sets the determination condition that differs between a case where it has been determined that the target area belongs to the front-field-of-view area and a case where it has been determined that the target area belongs to the side-field-of-view area.

6. The image processing device as defined in claim 5, wherein:

the evaluation value calculation section calculates an inter-frame difference value of the captured image as the evaluation value, and the determination section determines that the inter-frame state of the object is the stationary state when it has been determined that the target area belongs to the side-field-of-view area, and the inter-frame difference value is equal to or smaller than the estimated noise amount, and the determination section also determines that the inter-frame state of the object is the stationary state when it has been determined that the target area belongs to the front-field-of-view area, and the inter-frame difference value is equal to or smaller than a value obtained by multiplying the estimated noise amount by a coefficient that is larger than 1.

7. The image processing device as defined in claim 5, wherein the area determination section determines an area to which the target area belongs based on a position of the target area within the captured image.

8. The image processing device as defined in claim 1, wherein the determination section sets a determination condition for determining whether or not the inter-frame state of the object is the stationary state corresponding to the type of the captured image.

9. The image processing device as defined in claim 8, wherein:

the captured image is the white light image which includes information within a white wavelength band, or the special light image which includes information within a specific wavelength band, and the determination section sets the determination condition that differs between a case where the captured image is the white light image and a case where the captured image is the special light image.

10. The image processing device as defined in claim 9, wherein:

the evaluation value calculation section calculates an inter-frame difference value of the captured image as the evaluation value, and the determination section determines that the inter-frame state of the object is the stationary state when the captured image is the white light image, and the inter-frame difference value is equal to or smaller than the estimated noise amount, and the determination section also determines that the inter-frame state of the object is the stationary state when the captured image is the special light image, and the inter-frame difference value is equal to or smaller than a value obtained by multiplying the estimated noise amount by a coefficient that is smaller than 1.

11. The image processing device as defined in claim 9, wherein the specific wavelength band is narrower than the white wavelength band.

12. The image processing device as defined in claim 11, wherein:

the white light image and the special light image are each an in vivo image, and the specific wavelength band included in the in vivo image is a wavelength band of light absorbed by hemoglobin in blood.

13. The image processing device as defined in claim 12, wherein the specific wavelength band is 390 to 445 nm or 530 to 550 nm.

14. The image processing device as defined in claim 1, further comprising:
a motion vector detection section that detects a motion vector of the object within the captured image between a first frame and a second frame,
wherein:
the evaluation value calculation section calculates the evaluation value that is used to determine whether or not the inter-frame state of the object is the stationary state between the first frame and the second frame that is subjected to motion compensation using the motion vector, and
the noise reduction processing section performs the first noise reduction process and the second noise reduction process based on the first frame and the second frame that is subjected to motion compensation using the motion vector.

15. The image processing device as defined in claim 1, wherein:
the evaluation value calculation section calculates an inter-frame difference value of the captured image as the evaluation value, and
the determination section uses the estimated noise amount as a threshold value, and determines that the inter-frame state of the object is the stationary state when the inter-frame difference value is equal to or smaller than the threshold value.

16. The image processing device as defined in claim 15, wherein an area of the captured image in a first frame that is situated around a processing target pixel and has a given size is defined as a first area, and an area of the captured image in a second frame that is situated around the processing target pixel and has the given size is defined as a second area,
the evaluation value calculation section calculates a plurality of difference values between a pixel value of the first area and a pixel value of the second area while sequentially shifting the second area by one pixel relative to the first area in a horizontal direction and a vertical direction, and outputting a minimum value among the plurality of difference values as the inter-frame difference value, and
the determination section determines that the inter-frame state of the object is the stationary state when the minimum value is equal to or smaller than the threshold value.

17. An endoscope system comprising:
an imaging section that captures a captured image;
an evaluation value calculation section that calculates an evaluation value that is used to determine whether or not an inter-frame state of an object within the captured image is a stationary state;
an estimated noise amount acquisition section that acquires an estimated noise amount of the captured image;
a determination section that determines whether or not the inter-frame state of the object is the stationary state based on the evaluation value, the estimated noise amount, and a specific condition; and
a noise reduction processing section that performs a first noise reduction process that is a time-direction noise reduction process on the captured image when it has been determined that the inter-frame state of the object is the stationary state, and performs a second noise reduction process that includes at least a spatial-direction noise reduction process on the captured image when it has been determined that the inter-frame state of the object is not the stationary state,
wherein the determination section uses, as the specific condition, one of (i) angle-of-view information about an imaging section that captures the captured image, (ii) whether a target area of a noise reduction process belongs to a front-field-of-view area or a side-field-of-view area, and (iii) whether a type of the captured image belongs to a white light image or a special light image.

18. An image processing method comprising:
calculating an evaluation value that is used to determine whether or not an inter-frame state of an object within a captured image is a stationary state;
acquiring an estimated noise amount of the captured image;
determining whether or not the inter-frame state of the object is the stationary state based on the evaluation value, the estimated noise amount, and a specific condition, the specific condition being one of (i) angle-of-view information about an imaging section that captures the captured image, (ii) whether a target area of a noise reduction process belongs to a front-field-of-view area or a side-field-of-view area, and (iii) whether a type of the captured image belongs to a white light image or a special light image; and
performing a first noise reduction process that is a time-direction noise reduction process on the captured image when it has been determined that the inter-frame state of the object is the stationary state, and performing a second noise reduction process that includes at least a spatial-direction noise reduction process on the captured image when it has been determined that the inter-frame state of the object is not the stationary state.

19. A non-transitory computer-readable storage device with an executable program stored thereon, the program being executable by a computer to cause the computer to perform functions comprising:
calculating an evaluation value that is used to determine whether or not an inter-frame state of an object within a captured image is a stationary state;
acquiring an estimated noise amount of the captured image;
determining whether or not the inter-frame state of the object is the stationary state based on the evaluation value, the estimated noise amount, and a specific condition, the specific condition being one of (i) angle-of-view information about an imaging section that captures the captured image, (ii) whether a target area of a noise reduction process belongs to a front-field-of-view area or a side-field-of-view area, and (iii) whether a type of the captured image belongs to a white light image or a special light image; and
performing a first noise reduction process that is a time-direction noise reduction process on the captured image when it has been determined that the inter-frame state of the object is the stationary state, and performing a second noise reduction process that includes at least a spatial-direction noise reduction process on the captured image when it has been determined that the inter-frame state of the object is not the stationary state.

20. The image processing device as defined in claim 1, wherein the type of the captured image is determined by a number of pixels of the captured image, a resolution, an exposure time when the captured image was captured, a frame rate, a type of a connected imaging section, characteristics of illumination light, or characteristics of an optical filter used for imaging.

* * * * *